US011286258B2

United States Patent
Altel et al.

(10) Patent No.: US 11,286,258 B2
(45) Date of Patent: Mar. 29, 2022

(54) NATURE-INSPIRED ANTICANCER AND ANTIBACTERIAL MOTIFS AND PHARMACEUTICAL COMPOSITION THEREOF

(71) Applicant: University of Sharjah, Sharjah (AE)

(72) Inventors: Taleb H. Altel, Sharjah (AE); Vunnam Srinivasulu, Sharjah (AE); Mawieh Hamad, Sharjah (AE); Hany Omar, Sharjah (AE); Shifaa Abdin, Sharjah (AE); Amjad Ali, Sharjah (AE); Farah Ibrahim Al-Marzooq, Sharjah (AE); Mohamad Hamad, Sharjah (AE); Imad Abu Yousef, Sharjah (AE); Amin Majdalawieh, Sharjah (AE)

(73) Assignee: University of Sharjah, Sharjah (AE)

( * ) Notice: Subject to any disclaimer, the term of this patent is extended or adjusted under 35 U.S.C. 154(b) by 73 days.

(21) Appl. No.: 16/842,263

(22) Filed: Apr. 7, 2020

(65) Prior Publication Data
US 2021/0317121 A1    Oct. 14, 2021

(51) Int. Cl.
| | | |
|---|---|---|
| *C07D 471/16* | (2006.01) | |
| *A61P 31/04* | (2006.01) | |
| *A61P 35/00* | (2006.01) | |

(52) U.S. Cl.
CPC ............ *C07D 471/16* (2013.01); *A61P 31/04* (2018.01); *A61P 35/00* (2018.01)

(58) Field of Classification Search
CPC ......... A61P 31/04; A61P 35/00; C07D 471/16
See application file for complete search history.

(56) References Cited

U.S. PATENT DOCUMENTS

2021/0179605 A1*  6/2021  Altel .................... C07D 498/14

FOREIGN PATENT DOCUMENTS

WO    WO-2020021489 A2 *  1/2020  ........... C07D 498/14

OTHER PUBLICATIONS

Denizot; Synthesis 2018, 50, 4823-4828. DOI: 10.1055/s-0036-1592002 (Year: 2018).*
Kouznetsov; Tetrahedron Letters 2002, 43, 4707-4709. DOI: 10.1016/S0040-4039(02)00847-X (Year: 2002).*
Srinivasulu; Nature Communications 2018, 9, 4989. DOI: 10.1038/s41467-018-07521-2 (Year: 2018).*
Srinivasulu; J. Org. Chem. 2021, 86, 18, 12872-12885. DOI: 10.1021/acs.joc.1c01523 (Year: 2021).*

* cited by examiner

*Primary Examiner* — Daniel R Carcanague
(74) *Attorney, Agent, or Firm* — Hayes Soloway P.C.

(57) ABSTRACT

There is provided novel anticancer and antibacterial compounds, pharmaceutically acceptable salts thereof, and processes for their preparation. The compounds have anticancer activity, which results in the reduction of tumour cell proliferation, enhances cancers cells apoptosis and regulation of iron signalling. The compounds are also particularly active against various Gram-negative and Gram-positive multi-drug-resistant bacteria, such as extended-spectrum beta-lactamase (ESBL) producing and colistin-resistant *Escherichia coli*, carbapenem-resistant *E. coli*, carbapenem-resistant *Acinetobacter baumannii*, and methicillin-resistant *Staphylococcus aureus* (MRSA) including those with reduced susceptibility to many control antibiotics.

17 Claims, 11 Drawing Sheets

NATURE-INSPIRED ANTICANCER AND ANTIBACTERIAL MOTIFS AND PHARMACEUTICAL COMPOSITION THEREOF

FIELD OF THE INVENTION

The present invention provides for the synthesis of novel anticancer and antibacterial compounds, pharmaceutically acceptable salts thereof, and processes for their preparation. The compounds of the present invention are particularly active against various Gram-negative and Gram-positive multidrug-resistant bacteria, such as extended-spectrum beta-lactamase (ESBL) producing and colistin-resistant *Escherichia coli*, carbapenem-resistant *E. coli*, carbapenem-resistant *Acinetobacter baumannii*, and methicillin-resistant *Staphylococcus aureus* (MRSA) including those with reduced susceptibility to many control antibiotics.

BACKGROUND OF THE INVENTION

Background description includes information that may be useful in understanding the present invention. It is not an admission that any of the information provided herein is prior art or relevant to the presently claimed invention, or that any publication specifically or implicitly referenced is prior art.

Cancer metastasis is one of the leading causes of cancer-associated death in patients. Cancer patients with secondary metastasis often show recurrence and relapse. Clinically, cancer is a heterogeneous disease and in most cases, patients developing local and distant metastasis within 5 years of initial diagnosis eventually die as a result of cancer. The main options for treatment include chemotherapy, radiotherapy and surgery. Given the complexity and heterogeneity of solid tumors, chemotherapy remains the major treatment option in such patients. That said, chemotherapy often induces resistance resulting from the amplification of proteins involved in cell growth survival. Tumor growth is often associated with loss of function of tumor suppressor genes (TSGs) and/or gain of function of oncogenic proteins. Solid tumors undergo several genetic and epigenetic changes that create a microenvironment where resistance to chemotherapy promotes cancer progression, invasion and metastasis. Recently, anti-cancer drugs have been shown to induce kinome reprogramming in several human cancer cells. Therefore, the development of novel anti-cancer agents capable of overcoming resistance while minimizing chemotherapy-associated side effects remains a top priority in cancer research. In this regard, natural products and nature-inspired synthetic compounds that target previously unexploited features of disease-relevant proteins are considered to be effective modalities.

Over the past decades, the frequency of antimicrobial resistance has increased globally due to the misuse and overuse of antibiotics. Multidrug-resistant bacteria can cause different types of infections, such as pneumonia, urinary tract, bloodstream and wound infections, and are associated with high mortality and morbidity. The World Health Organization (WHO) has announced a list of 12 families of multidrug-resistant bacteria that pose a serious threat to human health. The list highlights, in particular, the threat of Gram-negative bacteria that are resistant to a large number of antibiotics, including carbapenems and cephalosporins, the best available antibiotics for treating multi-drug resistant bacteria. On top of this list is carbapenem-resistant *Acinetobacter baumannii*, and carbapenem-resistant, ESBL-producing Enterobacteriaceae, such as *E. coli*. Unfortunately, some of these bacteria also become resistant to colistin which is considered as one of the last-resort antibiotics for multidrug-resistant infections, despite its high nephrotoxicity. In addition to Gram-negative bacteria, there are clinically multidrug-resistant Gram-positive bacteria that were listed by the WHO as priority pathogens, including *Staphylococcus aureus*, those that are resistant to methicillin, and intermediately resistant or fully resistant to vancomycin.

Currently, there are very limited therapeutic options available to combat these highly resistant MDR bacteria. Accordingly, there exists a need to discover new antimicrobial agents with potent activity against multidrug-resistant organisms.

SUMMARY OF THE INVENTION

Therefore it is an objective of the present invention to provide for a compound with potent activity against multi-drug-resistant organisms.

In one aspect the present invention provides for novel anticancer and antibacterial compounds of general formula general formula (A)

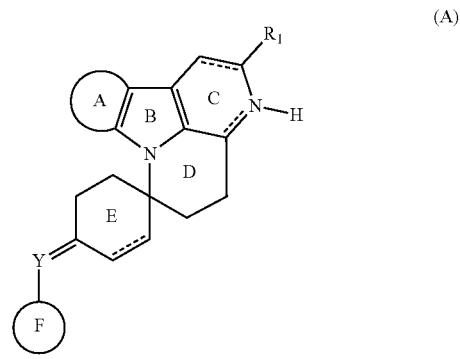

wherein:

is a phenyl ring which may be unsubstituted or substituted with 1, 2, 3, or 4 substituents independently selected from the group consisting of: a halogen atom, CN, $R^2$, $OR^2$, $SR^2$, $N(R^2)_2$, $C(O)R^2$, $C(O)OR^2$, $NR^2C(O)R^2$, $C(O)NR^2$, $SO_2R^2$, $NR^2SO_2R^2$, and $SO_2N(R^2)_2$;

is a phenyl ring which may be unsubstituted or substituted with 1, 2, 3, 4 or 5 substituents independently selected from the group consisting of: a halogen atom, CN, $NO_2$, $OCX_3$, $C(O)R^2$, $C(O)OR^2$, $NR^2C(O)R^2$, $C(O)NR^2$, $SO_2R^2$, $NR^2SO_2R^2$, and $SO_2N(R^2)_2$;

$R^1$ is hydrogen or an unsubstituted or substituted alkyl, aryl, or heteroaryl group or R[1] is selected from the group consisting of: C(O)OR[2], CN, N(R[2])$_2$, C(O)R[2], C(O)NR[2], SO$_2$R[2], SO$_2$N(R[2])$_2$, and PO$_2$R[2]; Y is —N—NR[2], —O or —OH;

R[2] is hydrogen or a substituted group selected from the group consisting of a C1-6 aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur; or a pharmaceutically acceptable salt, thereof In some embodiments, R2 is selected from the group consisting of: —CX3, —CHX2, and CH2X, wherein X is chlorine, fluorine, bromine, or iodine.

In addition to compounds having the general formula (A), enantiomers, diastereoisomers, racemates, pharmaceutically acceptable salts thereof are also within the scope of the present invention.

In a another embodiment, the present invention provides a novel synthetic method for the preparation of compounds of the general formula A and pharmaceutical compositions thereof The process for preparation of the compound of general formula A comprises using of compounds of general formulas (I), and (II), wherein general formula (I) is:

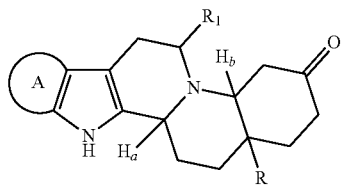

(I)

and general formula (II) is:

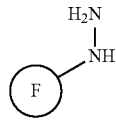

(II)

wherein

is a phenyl ring which may be unsubstituted or substituted with 1, 2, 3, or 4 substituents independently selected from the group consisting of: a halogen atom, CN, R[2], OR[2], SR[2], N(R[2])$_2$, C(O)R[2], C(O)OR[2], NR[2]C(O)R[2], C(O)NR[2], SO$_2$R[2], NR[2]SO$_2$R[2], and SO$_2$N(R[2])$_2$;

is a phenyl ring which may be unsubstituted or substituted with 1, 2, 3, 4 or 5 substituents independently selected from the group consisting of: a halogen atom, CN, NO$_2$, OCX$_3$, C(O)R[2], C(O)OR[2], NR[2]C(O)R[2], C(O)NR[2], SO$_2$R[2], NR[2]SO$_2$R[2], and SO$_2$N(R[2])$_2$;

R denotes halogen atom, R[2], OR[2], SR[2], N(R[2])$_2$, NR[2]C(O)R[2], C(O)NR[2], SO$_2$R[2], NR[2]SO$_2$R[2], SO$_2$N(R[2])$_2$;

R[1] is hydrogen or an unsubstituted or substituted alkyl, aryl, or heteroaryl group or R[1] is selected from the group consisting of: C(O)OR[2], CN, N(R[2])$_2$, C(O)R[2], C(O)NR[2], SO$_2$R[2], SO$_2$N(R[2])$_2$, and PO$_2$R[2];

R2 is hydrogen or a substituted group selected from the group consisting of: a C1-6 aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur; and the stereochemical relation between Ha, Hb, R and R1 is either in the form of pure enantiomers, diastereoisomers or racemic mixtures.

The process of preparing compound of general formula (A) further comprises reacting a compound of general formula (I)

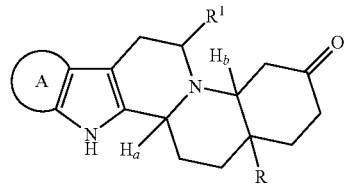

with the compound of general formula (II)

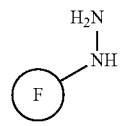

with acetic acid forming a mixture, thereafter heating the mixture between 40° C. to 150° C. obtaining a crude material and thereafter removing the solvent and purifying the obtained crude material on a column chromatography using a gradient of MeOH/DCM or EtOAc/hexane as mobile phase eluents, to yield a compound of general formula (A). During the process of preparation the mole ratio of compound of formula (I) to compound of formula (II) is about 1:1 to about 1:2. Further, the mobile phase used for the column chromatography is selected from MeOH/DCM or EtOAc/hexane. Additionally the solvent used for the recrystallization procedure is selected from EtOAc or MeOH. Furthermore, a combination of solvents used for the precipitation is selected from EtOAc/diethylether or EtOAc/hexane.

In another embodiment, the present invention discloses pharmaceutical composition comprising compounds of general Formula (A) as an active ingredient, or a pharmaceutically acceptable salt thereof and pharmaceutically acceptable carrier for treating a subject suffering from or susceptible to cancer by administering a therapeutically effective amount of the composition to the subject in need thereof.

In yet another embodiment, the present invention provides methods of use of the compounds of general formula A in preparation of a medicament having anticancer activity. The cancer cell lines are selected from the group consisting of colorectal, liver, lung, breast, stomach and cervical.

Furthermore, the cancer cell lines are HCT-116, Hep3b, A549, MCF-7, SKOV3, SKBR3, MDA-MB-231, MDA-MB-468, JIMT1, AGS and Hela.

In yet another embodiment, the present invention provides methods of use of the compounds of general formula A in preparation of a medicament having antibacterial activity. The bacterial species are selected from the group consisting of Gram-positive multidrug resistant bacteria, Gram-negative multidrug resistant bacteria and Gram-negative non-multidrug resistant bacteria. Preferably Gram-positive multidrug resistant bacteria are methicillin resistant *Staphylococcus aureus* ATCC33591, ATCC33592 and ATCC700699. Preferably Gram-negative multidrug resistant bacteria are carbapenem-resistant *E. coli* (ATCC BAA2469), colistin resistant *E. coli* (CDC-AR-0346) and carbapenem-resistant *Acinetobacter baumannii* (ATCC BAA1605). Preferably, Gram-negative non-multidrug resistant bacteria are *E. coli* (ATCC 25922) and *Acinetobacter baumannii* (ATCC 19606). the presently disclosed compounds have a killing effect on Gram-negative bacteria which includes extended-spectrum beta-lactamase (ESBL) and Gram-positive bacteria which includes methicillin-resistant *Staphylococcus aureus* (MRSA) and related *Staphylococcus* species.

In another embodiment the present disclosure provides methods of screening anticancer agents by treating a subject suffering from or susceptible to cancer or a different condition mediated by continuous cell proliferation. The disclosed methods of treatment include, in some embodiments, administering to a subject an effective amount of a compound or pharmaceutical composition described herein.

BRIEF DESCRIPTION OF THE DRAWINGS

The subject matter that is regarded as the invention is particularly pointed out and distinctly claimed in the claims at the conclusion of the specification. The foregoing and other aspects, features, and advantages of the invention are apparent from the following detailed description taken in conjunction with the accompanying drawings in which—

DETAILED DESCRIPTION OF THE INVENTION

Figure 1:
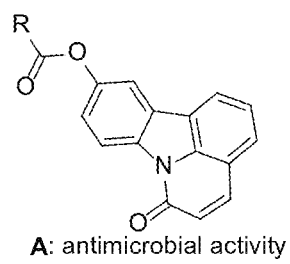
FIG. 1. depicts representative examples of bioactive canthinone alkaloid systems in accordance with an embodiment of the present invention.
Figure 1:
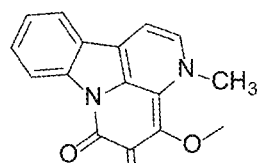
Figure 1:
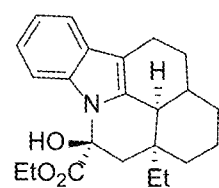
Figure 1:
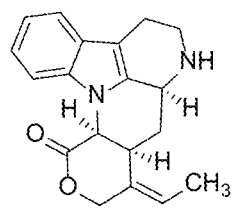
Figure 1:
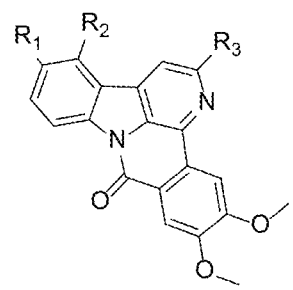
Figure 1:
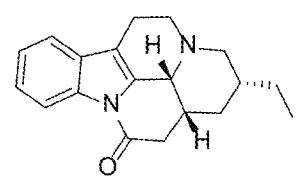
Figure 2A:
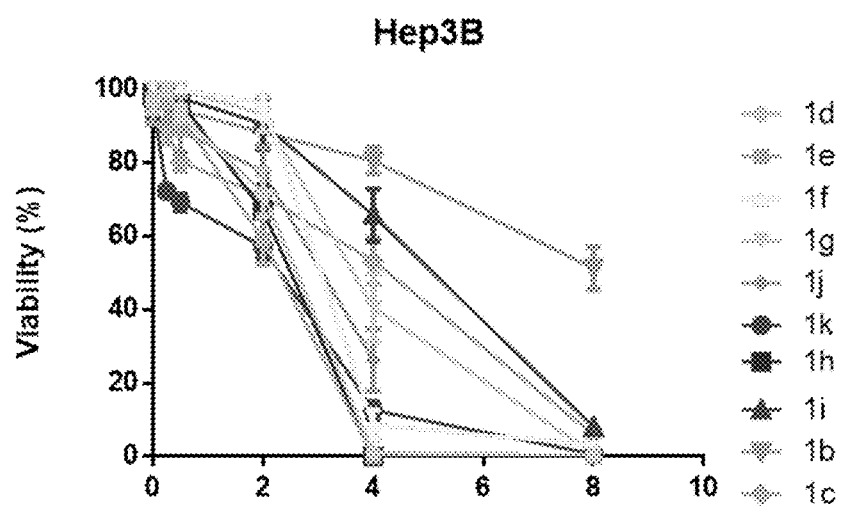
FIG. 2A. depicts a graphical representation showing IC50 calculations of novel compounds in normal and cancer cell lines (HCT-116): Full dose-response curves in accordance with an embodiment of the present invention.
Figure 2B:
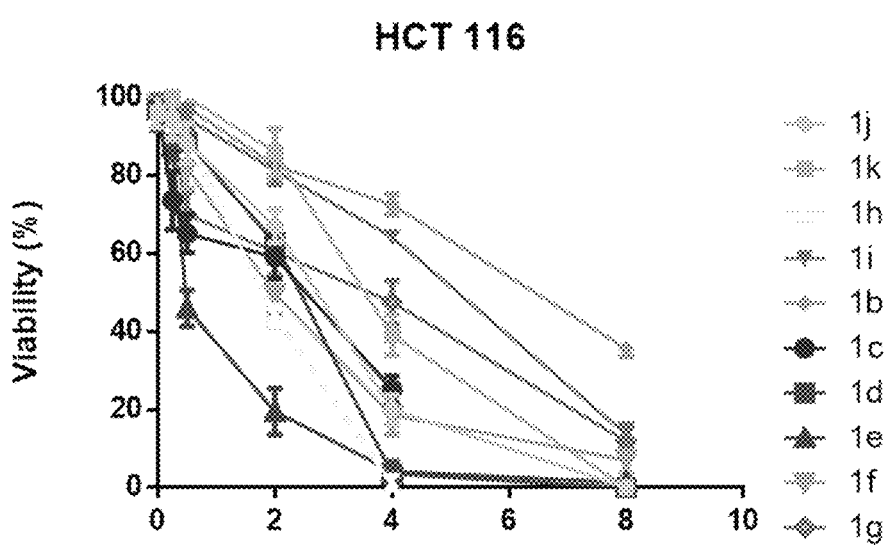
FIG. 2B. depicts a graphical representation showing IC50 calculations of novel compounds in normal and cancer cell lines (HELA): Full dose-response curves in accordance with an embodiment of the present invention.
Figure 2C:
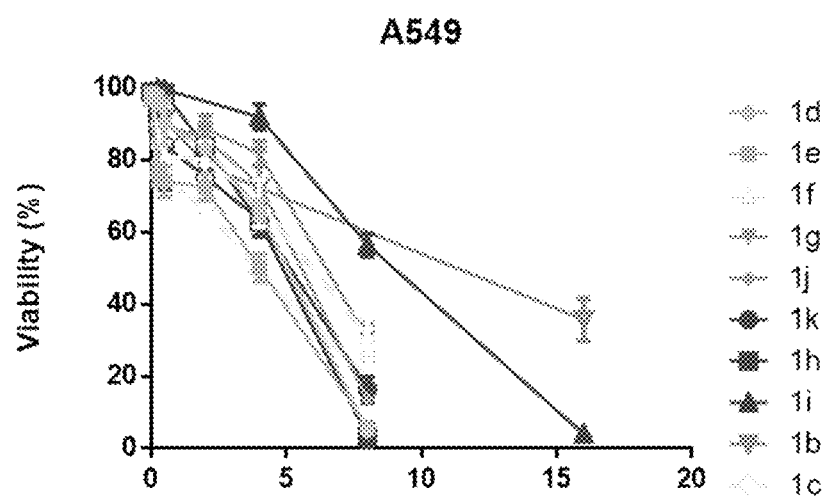
FIG. 2C. depicts a graphical representation showing IC50 calculations of novel compounds in normal and cancer cell lines (A549): Full dose-response curves in accordance with an embodiment of the present invention.
Figure 2D:
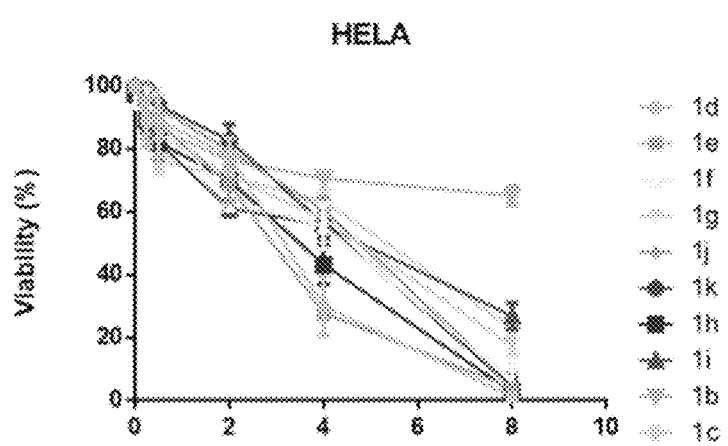
FIG. 2D. depicts a graphical representation showing IC50 calculations of novel compounds in normal and cancer cell lines (HEP3B): Full dose-response curves in accordance with an embodiment of the present invention.

The aspects of the present invention disclosing the synthesis of novel anticancer and antibacterial compounds, pharmaceutically acceptable salts thereof, and processes for their preparation, will be described in conjunction with FIGS. 1-5. In the Detailed Description, reference is made to the accompanying Figures, which form a part hereof, and in which is shown by way of illustration specific embodiments in which the invention may be practiced. It is to be understood that other embodiments may be utilized, and logical changes may be made without departing from the scope of the present invention. The following detailed description, therefore, is not to be taken in a limiting sense, and the scope of the present invention is defined by the appended claims.

The present invention provides for novel indolo-naphthyridine polycyclic ring systems of the general formula A, methods of preparing these systems, and uses of such novel compounds for different disease states, including as treatment agents for cell proliferative diseases and pathogenic infections. When discussing the disclosed compounds and compositions, the following terms have the following meaning unless otherwise indicated.

The term "aryl" means an aromatic or partially aromatic hydrocarbon group containing 6 to 10 carbon atoms and consisting of one or two rings that may be fused to each other or attached to each other via a single bond. Examples of aryl groups are phenyl, napthyl, biphenyl, and indenyl.

The term "heteroaryl," as used herein, means an aromatic or partially aromatic group consisting of one or two rings, which may be fused to each other or attached to each other via a single bond. A ring of a heteroaryl group may contain 5 to 10 ring atoms wherein up to four (e.g., one, two, three, or four) ring atoms are heteroatom(s) and the remaining ring atoms are carbon. Examples of heteroaryl groups include, but are not limited to: pyrrolyl, furyl, thienyl, oxazolyl, imidazolyl, purazolyl, isoxazolyl, isothiazolyl, triazolyl, thiadiazolyl, pyridyl, pyridazinyl, pyrimidinyl, pyrazinyl, pyranyl, furazanyl, indolizinyl, indolyl, isoindolinyl, indazolyl, benzofuryl, benzothienyl, benzimidazolyl, benzthiazolyl, purinyl, quinolizinyl, quinolinyl, isoquinolinyl, isothiazolyl, cinnolinyl, phthalazinyl, quinazolinyl, quinoxalinyl, naphthyridinyl, pteridinyl, and the like.

The term "alkyl," as used herein, denotes a saturated, linear, or branched chain hydrocarbon group containing 1 to 8 (e.g., 1 to 6 or 1 to 4) carbon atoms. For example, methyl, ethyl, propyl, isopropyl, 1-butyl, 2-butyl, and tert-butyl groups are alkyl groups. In select embodiments, "C1-C8 alkyl" groups have 1, 2, or 3 carbon atoms.

The term "halogen" means fluorine, chlorine, bromine, or iodine.

The term "substituted" means a group which may be substituted one to three times by a halogen atom, CN, R3, OR3, SR3, N(R3)2, C(O)R3, C(O)OR3, NR3C(O)R3, C(O)NR3, SO2R3, NR3SO$_2$R3, and/or SO2N(R3)2. With reference to substituents, the term "independently" means that when more than one of such substituents is possible, such substituents may be the same or different from one another.

The term "pharmaceutically acceptable carrier" or "pharmaceutically acceptable excipient" includes any and all solvents, dispersion media, coatings, antibacterial and antifungal agents, isotonic and absorption delaying agents and the like. The use of such media and agents for pharmaceutically active substances is well known in the art. Except insofar as any conventional media or agent is incompatible with the active ingredient, its use in the therapeutic compositions as disclosed herein is contemplated. Supplementary active ingredients can also be incorporated into the pharmaceutical compositions.

The term "pharmaceutically acceptable salt" refers to conventional acid-addition salts or base-addition salts that retain the biological effectiveness and properties of the compounds of the underlying chemical formula and are formed from suitable non-toxic organic or inorganic acids or organic or inorganic bases. Acid-addition salts include, for example, those derived from inorganic acids, such as hydrochloric acid, hydrobromic acid, hydroiodic acid, sulfuric acid, sulfonic acid, phosphoric acid, and nitric acid, and those derived from organic acids, such as p-toluenesulfonic acid, salicylic acid, methanesulfonic acid, oxalic acid, succinic acid, citric acid, malic acid, lactic acid, fumaric acid, and the like. Base-addition salts include those derived from ammonium, potassium, sodium and quaternary ammonium hydroxides, such as for example, tetramethyl ammonium hydroxide.

The compounds disclosed in the present invention may possess one or more asymmetric carbon atoms and are thus capable of existing in the form of optical isomers as well as in the form of racemic or non-racemic mixtures thereof. In some embodiments, the disclosed compounds may be utilized as a single isomer or as a mixture of stereochemical isomers. In embodiments in which diastereoisomers, i.e., nonsuperimposable stereochemical isomers, are used the diastereoisomers can be separated by any known technique, such as chromatography, distillation, crystallization, and/or sublimation. Optical isomers can be obtained by resolution of the racemic mixtures according to conventional processes, for example, by the formation of diastereoisomeric salts by treatment with an optically active acid or base. Examples of appropriate acids that may be used include, without limitation, tartaric, diacetyltartaric, dibenzoyltartaric, ditoluoyltartaric, and/or camphorsulfonic acid. A mixture of diastereomers can be separated by crystallization followed by the liberation of optically active bases from these salts. An alternative process for separation of optical isomers includes the use of a chiral chromatography column, which may be chosen to maximize the separation of the enantiomers.

In another aspect, the present invention also relates to the use of one or more of the disclosed compounds (at times referred to herein as "active ingredients") in the preparation of medicaments. In some embodiments, compounds of the formula A are administered either individually or in combination with any other desired therapeutic agent, using suitable delivery methods. The disclosed therapeutically useful agents may be administered, for example, by one of the following routes: orally, for example in the form of dragees, coated tablets, pills, semi-solid substances, soft or hard capsules, solutions, emulsions or suspensions; parenterally, for example, in the form of an injectable solution; rectally in the form of suppositories; by inhalation, for example, in the form of a powder formulation or a spray; and/or trans-dermally or intranasally. For the preparation of such tablets, pills, semi-solid substances, coated tablets, dragees, and hard gelatin capsules, the therapeutically usable product may be mixed with pharmacologically inert, inorganic or organic pharmaceutical carrier substances, for example, with lactose, sucrose, glucose, gelatin, malt, silica gel, starch or derivatives thereof, talcum, stearic acid or salts thereof, skimmed milk powder, and the like. For the preparation of soft capsules, pharmaceutical carrier substances such as, for example, vegetable oils, petroleum, animal or synthetic oils, wax, fat, and polyols may be used. For the preparation of liquid solutions and syrups, pharmaceutical carrier substances such as, for example, water, alcohols, aqueous saline solution, aqueous dextrose, polyols, glycerol, vegetable oils, petroleum, and animal or synthetic oils may be used. For suppositories, pharmaceutical carrier substances such as, for example, vegetable oils, petroleum, animal or synthetic oils, wax, fat, and polyols may be used. For aerosol formulations, compressed gases that are suitable for this purpose, such as, for example, oxygen, nitrogen and carbon dioxide may be used. The pharmaceutically acceptable agents may also comprise additives for preserving and stabilizing, emulsifiers, sweeteners, flavor rings, salts for altering the osmotic pressure, buffers, encapsulation additives and/or antioxidants. Numerous configurations and variations will be apparent to those skilled in the art upon consideration of the subject disclosure.

The term "anticancer" defines the use of natural/synthetic methods/substances for effective health care to contribute to and/or prevent the uncontrolled proliferation of tumor cells.

The term "proliferative" or "proliferation" in biological conditions refers to uncontrolled multiplication due to failure in the normal functioning of a system or a cell.

The term "effective amount" when used in connection with a compound of the general formula A means an amount of the subject compound effective for treating or preventing cancer or any other related or unrelated disease(s).

The term "full dose-response curve" is used herein with respect to multiple dosages of a compound to determine its response on a biological system, such as a cell-based model, to study the structural and functional relationship of a compound.

As used herein, the term "Multi-Drug Resistance (MDR)" is used in the context of the present invention to refer to a condition enabling disease-causing bacteria to resist distinct antibacterial compounds that are commonly used antibiotic drugs or commercially available antimicrobials agents.

The term "MIC" means a minimum inhibitory concentration, which is the lowest concentration of a chemical that is required to inhibit visible microbial growth following overnight incubation, usually reported in units of μg/mL.

The term "CFU" means colony-forming unit which is a unit used to estimate the number of viable microbial cells in a sample.

The term "resistant" or "resistance" to a bacterium or of a bacterial infection to an antibiotic includes a complete resistance to the antibiotic or a partial resistance, which is defined herein as a circumstance in which the MIC of an antibiotic toward the organism in question has increased.

As used herein, the following abbreviations have the following stated meanings:

EtOAc=Ethylacetate
DCM=Dicholoromethane
MeOH=Methanol
NMR=Nuclear magnetic resonance
HRMS=High resolution mass spectroscopy
LCMS=Liquid chromatography-mass spectroscopy
ESI-TOF=Electrosprayionization-time of flight The novel instant compounds of the present invention are particularly active against bacteria and bacteria-like microorganisms. The presently disclosed compounds are thus suitable for use in human and veterinary medicine, for example, for prophylaxis and/or chemotherapy of local and systemic infections caused by these pathogens.

An illustrative (but not exhaustive) list of pathogenic microorganisms that may be possible targets of the presently disclosed compounds is as follows: Gram-negative and Gram-positive multidrug-resistant bacteria, such as extended-spectrum beta-lactamase (ESBL) producing and colistin-resistant *Escherichia coli*, carbapenem-resistant *E. coli*, carbapenem-resistant *Acinetobacter baumannii*, and methicillin-resistant *Staphylococcus aureus* (MRSA) including those with reduced susceptibility to many control antibiotics.

The presently disclosed compounds may, in some embodiments, be formulated as pharmaceutical compositions and administered to a patient, such as a human patient, in a variety of forms adapted to the chosen route of administration, i.e., orally or parenterally, by intravenous, intra muscular, topical, and/or subcutaneous routes. In some embodiments, the disclosed antibacterial compounds may be administrated in combination with known antibiotics, including those with a different mechanism of action. The present disclosure provides novel indolo-naphthyridine polycyclic ring systems of the general formula A, methods of preparing these systems, and uses of such novel compounds for different disease states, including as treatment agents for cell proliferative diseases and pathogenic infections. The following experimental examples are included to provide further detail and are in no way intended to limit the scope of the present disclosure.

EXAMPLES

The examples and preparations provided below further illustrate and exemplify the compounds as provided herein and methods of preparing such compounds. It is to be understood that the scope of the present disclosure is not limited in any way by the scope of the following examples and preparations. In the following examples molecules with a single chiral center, unless otherwise noted, exist as a racemic mixture. Those molecules with two or more chiral centers, unless otherwise noted, exist as a racemic mixture of diastereomers. Single enantiomers/diastereomers can be obtained by methods known to those skilled in the art.

Example 1

In the first experimental example, novel compounds of the general formula A were prepared and characterized. The methods used to prepare these compounds and the resulting characterization data are provided below.

Ketone (general formula I, 0.5 mmol) and phenylhydrazine (general formula II, 0.5 mmol) were mixed in AcOH (2.0 mL) at room temperature and then refluxed it for 1-3 h. After completion, the solvent was removed under vacuum and concentrated to dryness. The crude material was purified on flash chromatography using EtOAc/hexane or MeOH/DCM as a mobile phase gradient to yield pure compounds of general formula A.

Compound 1a had the following chemical formula and characterization data:

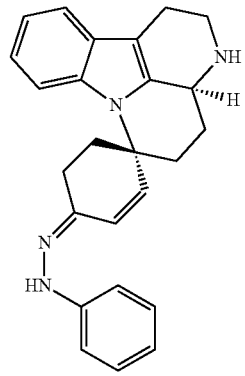

Compound 1a (1S,3a′S,Z)-4-(2-phenylhydrazono)-1′,2′,3′,3a′,4′,5′-hexahydrospiro[cyclohexane-1,6′-indolo[3,2,1-de][1,5]naphthyridin]-2-ene Brownish solid (112 mg, 59%). $^1$H NMR (500 MHz, DMSO-$d_6$) δ 9.26 (s, 1H), 7.50-7.33 (m, 2H), 7.25-7.14 (m, 4H), 7.05-6.95 (m, 2H), 6.76 (t, J=6.9 Hz, 1H), 6.42 (d, J=10.0 Hz, 1H), 6.24 (d, J=10.0 Hz, 1H), 3.97-3.90 (m, 1H), 3.05-2.96 (m, 1H), 2.93-2.85 (m, 1H), 2.78-2.69 (m, 1H), 2.68-2.60 (m, 1H), 2.42-2.31 (m, 1H), 2.29-2.17 (m, 2H), 2.03-1.90 (m, 3H), 1.72-1.61 (m, 1H). $^{13}$C NMR (125 MHz, DMSO-$d_6$) δ 145.5, 141.0, 137.0, 136.0, 135.1, 128.9, 128.5, 128.4, 120.3, 119.0, 119.0, 118.1, 112.7, 112.1, 104.8, 57.8, 52.1, 43.6, 31.2, 26.9, 24.2, 21.5, 21.2. HRMS (ESI-TOF): m/z calcd for $C_{25}H_{27}N_4$ 383.2235, found 383.2248 [M+H]$^+$.

Compound 1b had the following chemical formula and characterization data:

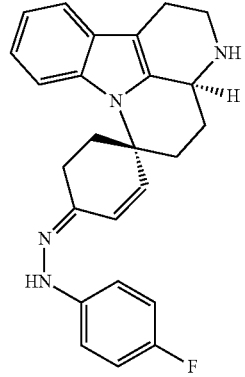

Compound 1b (1S,3a′S,Z)-4-(2-(4-fluorophenyl)hydrazono)-1′,2′,3′,3′a,4′,5′-hexahydrospiro[cyclohexane-1,6′-indolo[3,2,1-de][1,5]naphthyridin]-2-ene Brownish solid (106 mg, 53%). $^1$H NMR (500 MHz, DMSO-$d_6$) δ10.20 (s, 1H), 9.46 (s, 1H), 9.34 (s, 1H), 7.65-7.42 (m, 2H), 7.40-6.96 (m, 6H), 6.44 (d, J=10.0 Hz, 1H), 6.23 (d, J=10.0 Hz, 1H), 4.63-4.51 (m, 1H), 3.82-3.70 (m, 1H), 3.28-3.20 (m, 1H), 3.06-2.82 (m, 3H), 2.45-2.16 (m, 4H), 2.12-1.87 (m, 3H). $^{13}$C NMR (125 MHz, DMSO-d$_6$) δ 156.0 (d, 1JC-F=235 Hz), 142.2, 140.7, 135.9, 135.7, 129.3, 128.9, 127.3, 121.6, 119.7, 118.7, 115.3, 113.7, 112.4, 104.2, 57.9, 50.8, 42.0, 30.2, 26.9, 21.4, 21.2, 18.3. HRMS (ESI-TOF): m/z calcd for $C_{25}H_{26}FN_4$ 401.2141, found 401.2147 [M+H]$^+$.

Compound 1c had the following chemical formula and characterization data:

Compound 1c

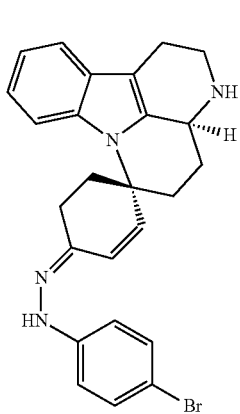

(1S,3a′S,Z)-4-(2-(4-bromophenyl)hydrazono)-1′,2′,3′,3′a,4′,5′-hexahydrospiro[cyclohexane-1,6′-indolo[3,2,1-de][1,5]naphthyridin]-2-ene Brownish solid (140 mg, 61%). $^1$H NMR (500 MHz, CD$_3$OD) δ 7.59 (d, J=8.2 Hz, 1H), 7.53 (d, J=7.6 Hz, 1H), 7.37-7.31 (m, 2H), 7.20-7.14 (m, 1H), 7.14-7.09 (m, 3H), 6.53 (d, J=10.0 Hz, 1H), 6.32 (d, J=10.0 Hz, 1H), 4.73-4.67 (m, 1H), 3.95-3.89 (m, 1H), 3.65-3.55 (m, 1H), 3.21-3.10 (m, 2H), 2.91-2.85 (m, 1H), 2.54-2.41 (m, 3H), 2.38-2.31 (m, 1H), 2.22-2.13 (m, 1H), 2.11-2.05 (m, 1H), 2.05-1.99 (m, 1H). $^{13}$C NMR (125 MHz, CD$_3$OD) δ 146.2, 142.7, 137.8, 137.5, 132.8, 130.5, 129.1, 129.0, 123.3, 121.3, 119.8, 115.8, 113.9, 112.4, 105.8, 59.4, 53.3, 44.6, 31.8, 28.3, 23.2, 22.0, 19.7. HRMS (ESI-TOF): m/z calcd for $C_{25}H_{26}BrN_4$ 461.1340, found 461.1342 [M+H]$^+$.

Compound 1d had the following chemical formula and characterization data:

Compound 1d

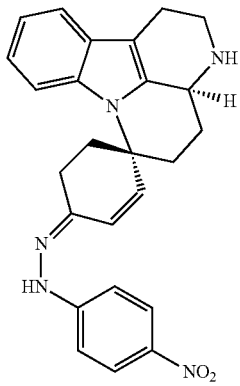

(1S,3a′S,Z)-4-(2-(4-nitrophenyl)hydrazono)-1′,2′,3′,3′a,4′,5′-hexahydrospiro[cyclohexane-1,6′-indolo[3,2,1-de][1,5]naphthyridin]-2-ene Yellowish solid (74 mg, 35%). $^1$H NMR (500 MHz, DMSO-d$_6$) δ 10.21 (s, 1H), 8.14 (d, J=8.9 Hz, 2H), 7.41 (t, J=8.0 Hz, 2H), 7.30 (d, J=8.8 Hz, 2H), 7.08-6.96 (m, 2H), 6.46 (q, J=10.0 Hz, 2H), 4.08-3.99 (m, 1H), 3.12-3.06 (m, 1H), 3.01-2.94 (m, 1H), 2.84-2.62 (m, 3H), 2.46-2.38 (m, 1H), 2.32-2.21 (m, 2H), 2.09-1.92 (m, 3H), 1.76-1.66 (m, 1H). $^{13}$C NMR (125 MHz, DMSO-d$_6$) δ 150.9, 146.0, 140.3, 140.2, 138.7, 135.1, 128.3, 127.9, 125.9, 120.6, 119.2, 118.2, 112.1, 112.0, 104.8, 57.7, 51.9, 43.4, 30.7, 26.8, 23.8, 21.6, 21.0. HRMS (ESI-TOF): m/z calcd for $C_{25}H_{26}N_5O_2$ 428.2086, found 428.2102 [M+H]$^+$.

Compound 1e had the following chemical formula and characterization data:

Compound 1e

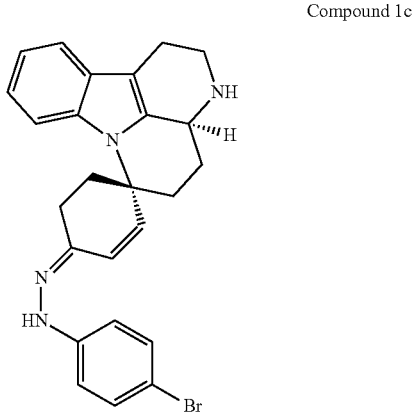

(1S,3a′S,Z)-4-(2-(4-trifluoromethyl)phenyl)hydrazono)-1′,2′,3′,3′a,4′,5′-hexahydrospiro[cyclohexane-1,6′-indolo[3,2,1-de][1,5]naphthyridin]-2-ene Brownish solid (146 mg, 65%). $^1$H NMR (500 MHz, DMSO-d$_6$) δ 9.73 (s, 1H), 7.53 (d, J=8.6 Hz, 2H), 7.42 (d, J=8.6 Hz, 2H), 7.31 (d, J=8.5 Hz, 2H), 7.08-6.96 (m, 2H), 6.44 (d, J=10.0 Hz, 1H), 6.33 (d, J=10.0 Hz, 1H), 4.12-4.04 (m, 1H), 3.52-3.45 (m, 1H), 3.13-3.06 (m, 1H), 2.97-2.89 (m, 1H), 2.86-2.75 (m, 1H), 2.75-2.68 (m, 1H), 2.47-2.36 (m, 1H), 2.31-2.21 (m, 2H), 2.08-2.01 (m, 1H), 2.01-1.93 (m, 2H), 1.79-1.67 (m, 1H). $^{13}$C NMR (125 MHz, DMSO-d$_6$) δ 148.5, 143.3, 138.5, 135.2, 134.4, 128.3, 128.2, 126.3, 125.0 (q, 1JC-F=268.7 Hz), 120.7, 119.2, 118.7, 118.3, 112.4, 112.2, 104.7, 57.7, 51.8, 43.3, 30.8, 26.9, 23.6, 21.4, 20.7. HRMS (ESI-TOF): m/z calcd for $C_{26}H_{26}F_3N_4$ 451.2109, found 451.2114 [M+H]$^+$.

Compound 1f had the following chemical formula and characterization data:

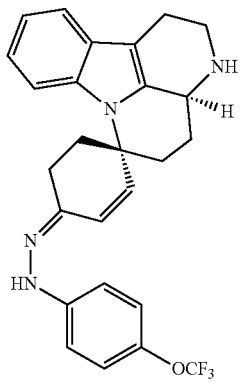

Compound 1f (1S,3a′S,Z)-4-(2-(4-(trifluoromethoxy)phenyl)hydrazono)-1′,2′,3′,3a′,4′,5′-hexahydrospiro[cyclohexane-1,6′-indolo[3,2,1-de][1,5]naphthyridin]-2-ene Brownish solid (144 mg, 62%). $^1$H NMR (500 MHz, DMSO-$d_6$) δ 10.24 (s, 1H), 9.56 (s, 1H), 9.49 (s, 1H), 7.52-7.45 (m, 2H), 7.28-7.22 (m, 2H), 7.22-7.18 (m, 2H), 7.15-7.03 (m, 2H), 6.45 (d, J=10.0 Hz, 1H), 6.27 (d, J=10.0 Hz, 1H), 4.63-4.53 (m, 1H), 3.80-3.71 (m, 1H), 3.44-3.36 (m, 1H), 3.09-2.87 (m, 3H), 2.47-2.35 (m, 1H), 2.35-2.29 (m, 1H), 2.28-2.21 (m, 2H), 2.09-1.98 (m, 2H), 1.98-1.91 (m, 1H). $^{13}$C NMR (125 MHz, DMSO-$d_6$) δ 145.2, 142.2, 141.3, 137.1, 136.2, 129.8, 129.3, 127.8, 122.5, 122.1, 120.8 (q, 1JC-F=254.5 Hz), 120.2, 119.2, 113.9, 112.9, 104.8, 58.3, 51.2, 42.5, 30.6, 27.4, 21.9, 21.8, 18.8. HRMS (ESI-TOF): m/z calcd for $C_{26}H_{26}F_3N_4O$ 467.2058, found 467.2079 [M+H]$^+$.

Compound 1g had the following chemical formula and characterization data:

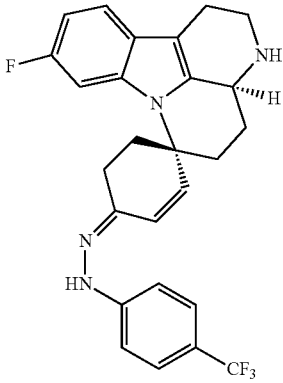

Compound 1g (1S,3a′S,Z)-9′-fluoro-4-(2-(4-(trifluoromethyl)phenyl)hydrazono)-1′,2′,3′,3a′,4′,5′-hexahydrospiro[cyclohexane-1,6′-indolo[3,2,1-de][1,5]naphthyridin]-2-ene Brownish solid (128 mg, 55%). $^1$H NMR (500 MHz, DMSO-$d_6$) δ10.24 (s, 1H), 9.83 (s, 1H), 9.52 (s, 1H), 7.58-7.47 (m, 3H), 7.33 (d, J=8.6 Hz, 2H), 7.21-7.16 (m, 1H), 6.98-6.92 (m, 1H), 6.49 (d, J=10.0 Hz, 1H), 6.30 (d, J=10.0 Hz, 1H), 4.61-4.52 (m, 1H), 3.79-3.71 (m, 1H), 3.03-2.91 (m, 3H), 2.48-2.38 (m, 1H), 2.36-2.29 (m, 1H), 2.28-2.19 (m, 2H), 2.10-1.91 (m, 3H). $^{13}$C NMR (125 MHz, DMSO-$d_6$) δ158.4 (d, 1JC-F=239.4 Hz), 148.5, 142.8, 136.8, 135.5, 129.9, 129.2, 126.3, 125.1 (q, 1JC-F=269.6 Hz), 124.2, 119.8, 118.8, 112.4, 108.1, 105.0, 98.8, 58.1, 50.6, 42.0, 30.0, 26.7, 21.4, 21.3, 18.2. HRMS (ESI-TOF): m/z calcd for $C_{26}H_{25}F_4N_4$ 469.2015, found 469.2021 [M+H]$^+$.

Compound 1h had the following chemical formula and characterization data:

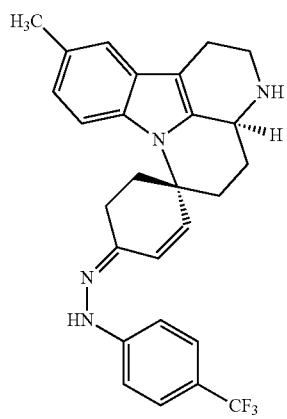

Compound 1h (1S,3a′S,Z)-10′-methyl-4-(2-(4-trifluoromethyl)phenyl)hydrazono)-1′,2′,3′,3a′,4′,5′-hexahydrospiro[cyclohexane-1,6′-indolo[3,2,1-de][1,5]naphthyridin]-2-ene Brownish solid (120 mg, 52%). $^1$H NMR (500 MHz, DMSO-$d_6$) δ 10.15 (s, 1H), 9.80 (s, 1H), 9.41 (s, 1H), 7.53 (d, J=8.4 Hz, 2H), 7.39-7.24 (m, 4H), 6.93 (d, J=8.3 Hz, 1H), 6.46 (d, J=10.0 Hz, 1H), 6.30 (d, J=10.0 Hz, 1H), 4.62-4.51 (m, 1H), 3.79-3.70 (m, 1H), 3.44-3.36 (m, 1H), 3.08-2.84 (m, 3H), 2.36 (s, 3H), 2.33-2.27 (m, 1H), 2.27-2.16 (m, 2H), 2.09-1.88 (m, 3H). $^{13}$C NMR (125 MHz, DMSO-$d_6$) δ 148.5, 143.0, 137.7, 134.1, 129.3, 128.6, 128.4, 127.6, 126.2, 125.0 (q, 1JC-F=269.6 Hz), 123.1, 118.9, 118.6, 118.4, 112.4, 112.1, 103.8, 57.7, 50.8, 42.0, 26.8, 21.4, 21.3, 21.0, 18.3. HRMS (ESI-TOF): m/z calcd for $C_{27}H_{28}F_3N_4$ 465.2266, found 465.2258 [M+H]$^+$.

Compound 1i had the following chemical formula and characterization data:

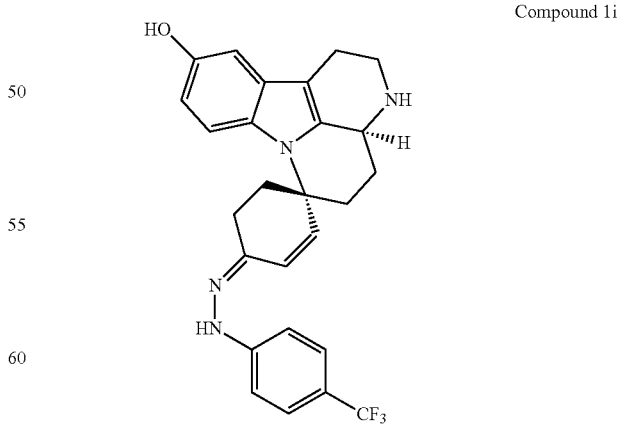

Compound 1i (1S,3a′S,Z)-4-(2-(4-trifluoromethyl)phenyl)hydrazono)-1′,2′,3′,3a′,4′,5′-hexahydrospiro[cyclohexane-1,6′-indolo[3,2,1-de][1,5]naphthyridin]-2-ene-10′-ol Brownish solid (135 mg, 58%). $^1$H NMR (500 MHz, DMSO-d$_6$) δ10.19 (s, 1H), 9.80 (s, 1H), 9.38 (s, 1H), 7.53 (d, J=8.5 Hz, 2H), 7.37-7.28 (m, J=8.4 Hz, 2H), 7.28-7.21 (m, 1H), 6.79 (s, 1H), 6.62 (d, J=8.8 Hz, 1H), 6.44 (d, J=10.0 Hz, 1H), 6.29 (d, J=10.0 Hz, 1H), 4.59-4.46 (m, 1H), 3.77-3.68 (m, 1H), 3.31-3.24 (m, 1H), 3.01-2.79 (m, 3H), 2.45-2.35 (m, 1H), 2.33-2.15 (m, 3H), 2.04-1.87 (m, 3H). $^{13}$C NMR (125 MHz, DMSO-d$_6$) δ 151.3, 148.5, 143.1, 137.9, 130.2, 129.6, 128.6, 128.3, 126.2, 125.0 (q, 1JC-F=269.6 Hz), 118.9, 118.6, 112.8, 112.4, 111.5, 103.5, 102.9, 57.6, 50.8, 42.0, 30.0, 26.9, 21.5, 18.3. HRMS (ESI-TOF): m/z calcd for C$_{26}$H$_{26}$F$_3$N$_4$O 467.2058, found 467.2059 [M+H]$^+$.

Compound 1j had the following chemical formula and characterization data:

Compound 1j

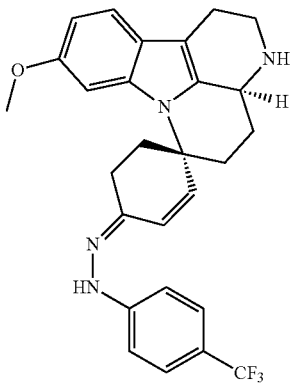

(1S,3a'S,Z)-9'-methoxy-4-(2-(4-trifluoromethyl)phenyl)hydrazono)-1',2',3',3'a,4',5'-hexahydrospiro[cyclohexane-1,6'-indolo[3,2,1-de][1,5]naphthyridin]-2-ene Brownish solid (146 mg, 61%). $^1$H NMR (500 MHz, DMSO-d$_6$) δ 10.20 (s, 1H), 9.81 (s, 1H), 9.42 (s, 1H), 7.53 (d, J=7.9 Hz, 1H), 7.39 (d, J=8.4 Hz, 1H), 7.33 (d, J=8.2 Hz, 1H), 6.95 (s, 1H), 6.76 (d, J=8.4 Hz, 1H), 6.48 (d, J=10.0 Hz, 1H), 6.32 (d, J=10.0 Hz, 1H), 4.57-4.46 (m, 1H), 3.78-3.65 (m, 4H), 3.42-3.37 (m, 1H), 3.04-2.88 (m, 3H), 2.46-2.37 (m, 1H), 2.33-2.17 (m, 2H), 2.07-1.86 (m, 3H). $^{13}$C NMR (125 MHz, DMSO-d$_6$) δ 155.4, 148.5, 143.0, 137.6, 136.6, 128.7, 128.0, 126.2, 125.0 (q, 1JC-F=268.7 Hz) 121.8, 119.3, 118.7, 112.4, 108.5, 104.3, 96.9, 57.7, 55.3, 50.7, 42.0, 40.0, 30.1, 26.5, 21.5, 18.3. HRMS (ESI-TOF): m/z calcd for C$_{27}$H$_{28}$F$_3$N$_4$O 481.2215, found 481.2213 [M+H]$^+$.

Compound 1k had the following chemical formula and characterization data:

Compound 1k

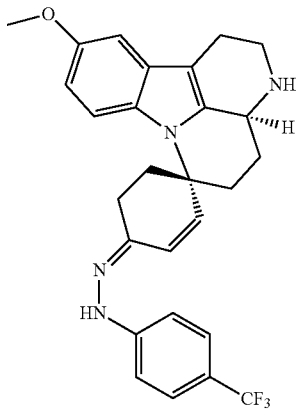

(1S,3a'S,Z)-10'-methoxy-4-(2-(4-trifluoromethyl)phenyl)hydrazono)-1',2',3',3'a,4',5'-hexahydrospiro[cyclohexane-1,6'-indolo[3,2,1-de][1,5]naphthyridin]-2-ene Brownish solid (141 mg, 59%). $^1$H NMR (500 MHz, Acetone-d$_6$) δ 9.14 (s, 1H), 7.52 (d, J=8.6 Hz, 2H), 7.39-7.30 (m, 3H), 6.92 (d, J=2.5 Hz, 1H), 6.67 (dd, J=8.9, 2.5 Hz, 1H), 6.47 (d, J=10.0 Hz, 1H), 6.36 (d, J=10.0 Hz, 1H), 3.99-3.91 (d, J=6.9 Hz, 1H), 3.77 (s, 3H), 3.50-3.42 (m, 1H), 3.16-3.11 (m, 1H), 3.09-3.03 (m, 1H), 2.94-2.85 (m, 1H), 2.82-2.74 (m, 1H), 2.67-2.60 (m, 1H), 2.51-2.41 (m, 1H), 2.37-2.28 (m, 1H), 2.26-2.20 (m, 1H), 2.02-1.89 (m, 2H), 1.77-1.66 (m, 1H). $^{13}$C NMR (126 MHz, Acetone-d$_6$) δ 155.0, 149.6, 144.2, 140.1, 131.8, 130.7, 129.2, 127.1, 124.0 (q, 1JC-F=259.5 Hz), 121.0, 113.6, 113.4, 113.4, 110.6, 106.3, 101.5, 58.8, 55.8, 53.6, 45.1, 32.3, 28.0, 25.7, 22.9, 21.8. HRMS (ESI-TOF): m/z calcd for C$_{27}$H$_{28}$F$_3$N$_4$O 481.2215, found 481.2224 [M+H]$^+$.

Compound 1l had the following chemical formula and characterization data:

Compound 1l

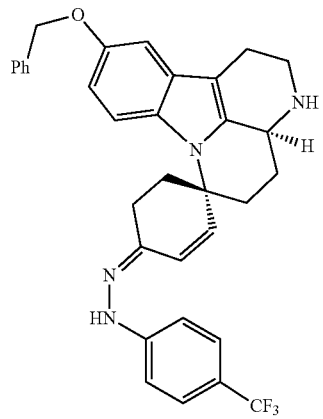

(1S,3a'S,Z)-10'-(benzyloxy)-4-(2-(4-(triflouromethyl)phenyl)hydrazono)-1',2',3',3a',4',5'-hexahydrospiro[cyclohexane-1,6'-indolo[3,2,1-de][1,5]naphthyridin]-2-ene Brownish solid (155 mg, 56%). $^1$H NMR (500 MHz, DMSO-d$_6$) δ10.19 (s, 1H), 9.81 (s, 1H), 9.44 (s, 1H), 7.53 (d, J=8.6 Hz, 2H), 7.41-7.36 (m, 2H), 7.35-7.29 (m, 3H), 7.15-7.09 (m, 1H), 7.11 (d, J=2.1 Hz, 1H), 6.87-6.80 (m, 1H), 6.46 (d, J=10.0 Hz, 1H), 6.30 (d, J=10.0 Hz, 1H), 5.14-5.06 (m, 2H), 4.60-4.49 (m, 1H), 3.79-3.70 (m, 1H), 3.04-2.87 (m, 3H), 2.47-2.36 (m, 1H), 2.33-2.26 (m, 1H), 2.26-2.16 (m, 2H), 2.09-1.87 (m, 4H). $^{13}$C NMR (126 MHz, DMSO-$d_6$) δ 152.8, 148.5, 143.0, 137.6, 137.5, 130.9, 130.0, 128.8, 128.4, 127.9, 127.7, 127.6, 126.2, 125.0 (q, 1JC-F=268.7 Hz), 118.7, 113.0, 112.4, 111.9, 104.1, 102.5, 69.7, 57.7, 50.8, 42.1, 40.0, 30.0, 27.0, 21.4, 18.4. HRMS (ESI-TOF): m/z calcd for $C_{33}H_{32}F_3N_4O$ 557.2528, found 557.2518 [M+H]$^+$.

Compound 1m had the following chemical formula and characterization data:

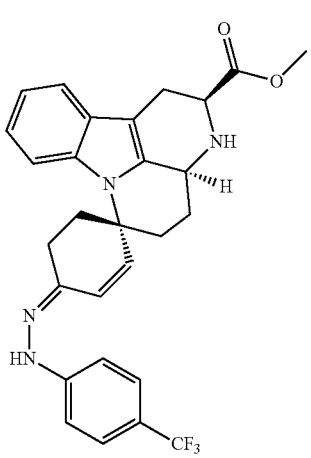

Compound 1m methyl (1S,2'S,3a'S,Z)-4-(2-(4-(trifluoromethyl)phenyl)hydrazono)-1',2',3',3a',4',5'-hexahydrospiro[cyclohexane-1,6'-indolo[3,2,1-de][1,5]naphthyridin]-2-ene-2'-carboxylate Yellowish solid (124 mg, 49%). $^1$H NMR (500 MHz, Acetone-$d_6$) δ 9.11 (s, 1H), 7.53 (d, J=8.6 Hz, 2H), 7.51-7.47 (m, 1H), 7.45-7.39 (m, 1H), 7.37-7.32 (m, 2H), 7.06-6.98 (m, 2H), 6.50 (d, J=10.0 Hz, 1H), 6.41 (d, J=10.0 Hz, 1H), 4.07-4.00 (m, 1H), 3.94-3.89 (m, 1H), 3.77 (s, 3H), 3.06-2.99 (m, 1H), 2.95-2.89 (m, 1H), 2.76-2.71 (m, 1H), 2.56-2.47 (m, 1H), 2.444-2.36 (m, 1H), 2.33-2.28 (m, 1H), 2.18-2.08 (m, 2H), 1.80-1.73 (m, 1H). $^{13}$C NMR (125 MHz, Acetone-$d_6$) δ 174.1, 149.6, 144.1, 139.8, 137.1, 129.8, 129.3, 127.1, 124.0 (q, 1JC-F=270.9 Hz), 121.4, 121.2, 121.0, 120.2, 119.0, 113.4, 113.3, 105.6, 59.1, 58.0, 53.1, 52.1, 32.4, 27.9, 26.3, 25.6, 21.8. HRMS (ESI-TOF): m/z calcd for $C_{28}H_{28}F_3N_4O_2$ 509.2164, found 509.2182 [M+H]$^+$.

Compound 1n had the following chemical formula and characterization data:

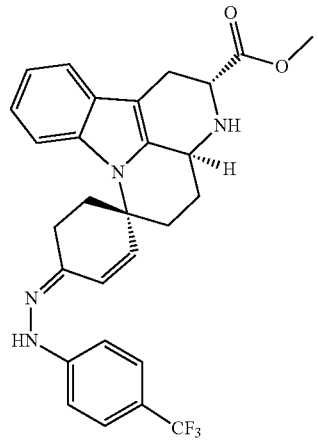

Compound 1n methyl (1S,2'R,3a'R,Z)-4-(2-(4-(triflouromethyl)phenyl)hydrazono)-1',2',3',3a',4',5'-hexahydrospiro[cyclohexane-1,6'-indolo[3,2,1-de][1,5]naphthyridin]-2-ene-2'-carboxylate Yellowish solid (119 mg, 47%). $^1$H NMR (500 MHz, Acetone-$d_6$) δ 9.10 (s, 1H), 7.53 (d, J=8.6 Hz, 2H), 7.51-7.47 (m, 1H), 7.45-7.41 (m, 1H), 7.35 (d, J=8.6 Hz, 2H), 7.07-6.99 (m, 2H), 6.50 (d, J=10.0 Hz, 1H), 6.40 (d, J=10.0 Hz, 1H), 4.06-3.99 (m, 1H), 3.94-3.88 (m, 1H), 3.77 (s, 3H), 3.06-2.99 (m, 1H), 2.95-2.88 (m, 2H), 2.79-2.71 (m, 2H), 2.56-2.45 (m, 1H), 2.44-2.35 (m, 1H), 2.34-2.26 (m, 1H), 2.15-2.08 (m, 1H), 2.03-1.99 (m, 1H), 1.81-1.70 (m, 1H). $^{13}$C NMR (125 MHz, Acetone-$d_6$) δ 174.1, 149.6, 144.1, 139.8, 137.2, 136.9, 129.8, 129.2, 127.2, 124.0 (q, 1JC-F=269.6 Hz), 121.4, 120.1, 118.9, 113.4, 113.2, 105.6, 59.1, 58.0, 53.1, 52.1, 32.4, 27.9, 26.3, 25.6, 21.7. HRMS (ESI-TOF): m/z calcd for $C_{28}H_{28}F_3N_4O_2$ 509.2164, found 509.2180 [M+H]$^+$.

Compound 1o had the following chemical formula and characterization data:

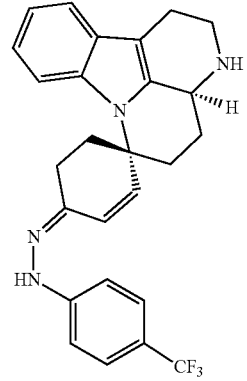

Compound 1o (1S,3a'S,E)-4-(2-(4-(triflouromethyl)phenyl)hydrazono)-1',2',3',3a',4',5'-hexahydrospiro[cyclohexane-1,6'-indolo[3,2,1-de][1,5]naphthyridine]

Compound (1e, 0.3 mmol) was dissolved in methanol (1.5 mL) and 10 wt % Pd/C (5 mol %) was added and stirring was continued under hydrogen atmosphere for 3-4 h at rt. After completion, the reaction mixture was filtered through a celite pad and the filtrate was concentrated. The crude was purified on flash chromatography, using MeOH in DCM as an eluent to produce the title compound 1o. Yellowish solid (111 mg, 82%). $^1$H NMR (500 MHz, DMSO-$d_6$) δ 10.22 (s, 1H), 9.56 (bs, 1H), 9.30 (s, 1H), 7.59 (t, J=7.7 Hz, 1H), 7.53-7.45 (m, 3H), 7.26-7.18 (d, J=8.2 Hz, 2H), 7.15-7.09 (m, 1H), 7.09-7.03 (m, 1H), 4.58-4.51 (m, 1H), 3.76-3.69 (m, 1H), 3.10-2.85 (m, 5H), 2.64-2.58 (m, 1H), 2.46-2.36 (m, 2H), 2.32-2.19 (m, 2H), 2.04-1.74 (m, 5H). HRMS (ESI-TOF): m/z calcd for $C_{26}H_{28}F_3N_4$ 453.2266, found 453.2279 [M+H]$^+$.

Compound 1p had the following chemical formula and characterization data:

Compound 1p

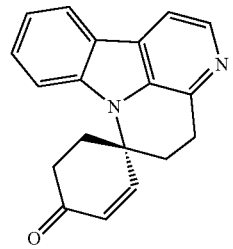

(S)-4',5'-dihydrospiro[cyclohexane-1,6'-indolo[3,2,1-de][1,5]naphthyridin]-2-en-4-one Compound 1e (0.5 mmol) was mixed in phosphoric acid (1.0 mL) and subjected to microwave irradiation (power 150 W and pressure 200 psi) at 80° C. for 2 min. After completion, the reaction mixture was quenched with saturated sodium bicarbonate solution and then diluted with ethylacetate (200 mL). The organic layer was separated, dried over $Na_2SO_4$ and concentrated under vacuum. The crude was purified on flash chromatography using 40% EtOAc/hexane as eluent to produce compound 1p as brownish solid (30 mg, 21%). $^1$H NMR (500 MHz, CD$_3$OD) δ 8.26-8.20 (m, 2H), 7.92 (d, J=5.4 Hz, 1H), 7.70 (d, J=8.4 Hz, 1H), 7.59-7.53 (m, 1H), 7.37 (dd, J=10.2, 2.0 Hz, 1H), 7.32 (t, J=7.5 Hz, 1H), 6.35 (d, J=10.2 Hz, 1H), 3.42-3.24 (m, 2H), 2.93-2.82 (m, 1H), 2.79-2.72 (m, 1H), 2.65-2.55 (m, 2H), 2.44-2.33 (m, 2H). $^{13}$C NMR (125 MHz, CD$_3$OD) δ 199.6, 156.0, 143.1, 141.0, 138.9, 134.3, 131.3, 129.6, 128.0, 123.8, 123.3, 121.4, 114.4, 112.5, 58.2, 35.1, 31.3, 30.8, 26.1. LCMS (ESI): m/z 289 [M+H]$^+$.

Compound 1q had the following chemical formula and characterization data:

Compound 1q

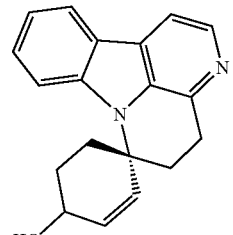

(1S)-4',5'-dihydrospiro[cyclohexane-1,6'-indolo[3,2,1-de][1,5]naphthyridin]-2en-4-ol Compound 1p (0.1 mmol) was dissolved in methanol (2.0 mL) and CeCl$_3$.7H$_2$O (0.1 mmol) was added at −20° C. Then, NaBH$_4$ (0.11 mmol) was added slowly and stirring was continued at −20° C. for 15 min. After completion, the reaction mixture was quenched with ice at 0° C. Then, the reaction mixture was diluted with EtOAc (30 mL) and washed with water (2×20 mL). The organic layer was separated, dried over Na$_2$SO$_4$ and concentrated under vacuum. The crude was purified on flash chromatography, using 60% EtOAc in hexane as an eluent to produce the title compound 1q. (Brownish solid, 24 mg, 83%). $^1$H NMR (500 MHz, CD$_3$OD) δ 8.20-8.12 (m, 2H), 7.85 (d, J=5.5 Hz, 1H), 7.78 (d, J=8.5 Hz, 1H), 7.55-7.48 (m, 1H), 7.28-7.23 (m, 1H), 6.16 (d, J=10.2 Hz, 1H), 5.99-5.84 (m, 1H), 4.56-4.43 (m, 1H), 3.27-3.11 (m, 2H), 2.60-2.53 (m, 1H), 2.23-1.98 (m, 4H), 1.90-1.79 (m, 1H). LCMS (ESI): m/z 291 [M+H]$^+$.

Example 2

In a second experimental example the compounds described in Example 1 were initially screened for their potential anticancer activities against various cancer and normal cell lines at a concentration of 5 μM. The full dose-response curves for representative compounds (1b-k) on the survival of five cancer cell lines (HCT-116, HELA, A549, HEP3B, and MCF-7) are displayed in FIG. 2 and the calculated IC$_{50}$ values are presented in Table 1 and Table 2. In addition, the effect of these compounds on the survival of normal epithelial cells was studied and the results are shown in Table 3. The new compounds appear to be relatively safe when tested in normal epithelial cells at high concentrations (10 μM).

Figure 3A:
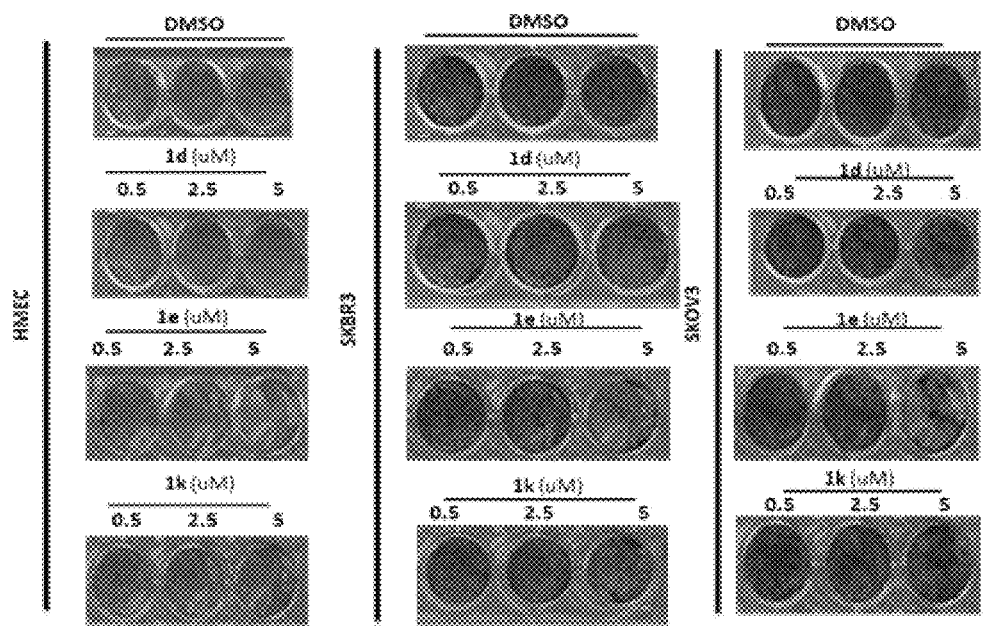
FIG. 3A. depicts an image of the crystal violet staining assay: Treatment of compounds 3033, 3058 and 3066 on HMEC, SKBR3, and SKOV3 cell lines in accordance with an embodiment of the present invention.
Figure 3B:
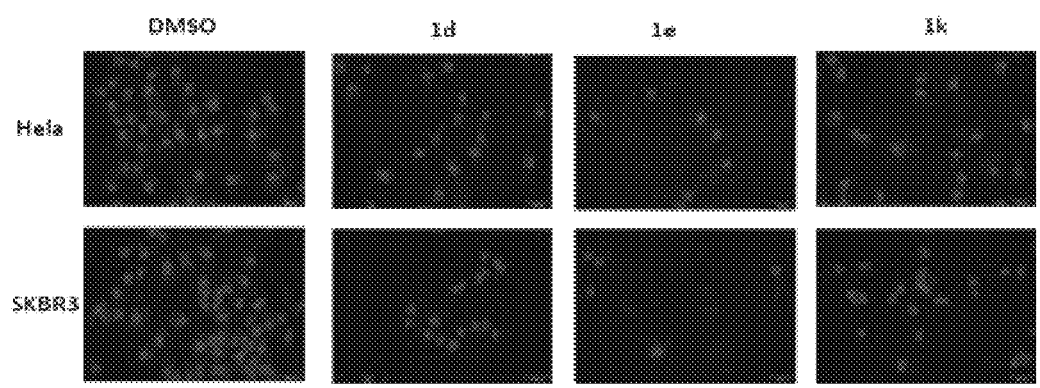
FIG. 3B. depicts an image of the DAPI staining assay: Treatment of compounds 3033, 3058 and 3066 on Hela and SKBR3 cell lines in accordance with an embodiment of the present invention.

Furthermore, crystal violet studies and DAPI staining results indicated the potency of these compounds on cancer cell lines SKBR3 and SKOV3 (as shown in FIG. 3). This data suggests that compound 1e induce greater levels of nuclear damage in the cancer cell lines compared to compounds 1d and 1k.

TABLE 1

IC$_{50}$ values for compounds 1b-1k tested against cell lines HCT-116, HELA, A549, HEP3B, MCF-7 and HMEC.

| Compound | IC$_{50}$ (μM)$^a$ | | | | |
| --- | --- | --- | --- | --- | --- |
| | HCT-116$^b$ | HELA$^c$ | A549$^d$ | HEP3B$^e$ | MCF-7$^f$ |
| 1b | 6.43 ± 0.03 | >10 | 10.25 ± 0.08 | 8 ± 0.07 | 6.22 ± 0.16 |
| 1c | 2.65 ± 0.05 | 5.304 ± 0.35 | 3.904 ± 0.04 | 4.212 ± 0.06 | 2.75 ± 0.06 |
| 1d | 2.49 ± 0.02 | 3.136 ± 0.04 | 5.22 ± 0.03 | 2.32 ± 0.16 | 3.088 ± 0.04 |
| 1e | 0.487 ± 0.03 | 2.565 ± 0.58 | 4.011 ± 0.02 | 2.03 ± 0.08 | 1.8614 ± 0.03 |
| 1f | 1.96 ± 0.05 | 3.889 ± 0.07 | 5.99 ± 0.03 | 2.642 ± 0.03 | 3.56 ± 0.1 |
| 1g | 3.02 ± 1.2 | 4.6254 ± 0.04 | 7.44 ± 0.04 | 3.597 ± 0.03 | 5.341 ± 1.8 |
| 1h | 1.78 ± 0.7 | 3.504 ± 0.06 | 4.897 ± 0.03 | 2.565 ± 0.07 | 3.724 ± 0.05 |
| 1i | 5.177 ± 0.02 | 4.075 ± 0.12 | 8.607 ± 0.02 | 5.132 ± 0.04 | 5.61 ± 0.08 |

TABLE 1-continued

IC$_{50}$ values for compounds 1b-1k tested against cell
lines HCT-116, HELA, A549, HEP3B, MCF-7 and HMEC.

| Compound | IC$_{50}$ (μM)[a] | | | | |
|---|---|---|---|---|---|
| | HCT-116[b] | HELA[c] | A549[d] | HEP3B[e] | MCF-7[f] |
| 1j | 2.3 ± 0.04 | 4.601 ± 0.03 | 5.607 ± 0.12 | 2.876 ± 0.14 | 3.00 ± 2.4 |
| 1k | 3.385 ± 0.04 | 4.514 ± 0.03 | 5.491 ± 0.05 | 2.2761 ± 0.01 | 3.572 ± 0.34 |

[a]50% Inhibitory concentration after 48 h of drug treatment and the values are average of three individual experiments,
[b]colon cancer,
[c]cervical cancer,
[d]lung cancer,
[e]liver cancer,
[f]breast cancer.

TABLE 2

IC$_{50}$ values for compounds 1d-e and 1k tested against cell lines SKOV3,
SKBR3, MDA-MB231, JIMT1, MDA-MB-468, and AGS.

| Compound | IC$_{50}$ (μM)[a] | | | | | |
|---|---|---|---|---|---|---|
| | SKOV3[b] | SKBR3[c] | MDA-MB-231[d] | JIMT1[e] | MDA-MB-468[f] | AGS[g] |
| 1d | 6.52 ± 0.20 | 3.93 ± 0.16 | 4.22 ± 0.10 | 4.00 ± 0.10 | 3.06 ± 0.17 | 5.37 ± 0.17 |
| 1e | 3.84 ± 0.21 | 1.96 ± 0.08 | 3.63 ± 0.06 | 3.08 ± 0.14 | 2.50 ± 0.13 | 3.31 ± 0.12 |
| 1k | 4.68 ± 0.22 | 4.10 ± 0.21 | 4.03 ± 0.16 | 3.49 ± 0.06 | 2.49 ± 0.16 | 4.66 ± 0.15 |

[a]50% Inhibitory concentration after 48 h of drug treatment. The values are the average of three individual experiments, [b,c,d,e,f]breast cancer, [g]stomach cancer.

TABLE 3

IC$_{50}$ values for compounds 1d-f and 1h-k tested
against normal epithelial cells (HMEC).

| Compound | IC$_{50}$ (μM)[a] |
|---|---|
| 1d | 42.04 ± 0.08 |
| 1e | 2.91 ± 0.07 |
| 1f | 18.38 ± 0.05 |
| 1h | 11.526 ± 0.04 |
| 1i | 12.70 ± 0.05 |
| 1j | 10.77 ± 0.05 |
| 1k | 28.01 ± 0.09 |

[a]50% Inhibitory concentration after 48 h of drug treatment. The values are the average of three individual experiments.

Example 3

In a third experimental example in an effort to further validate the anticancer effect of the disclosed compounds, various biological studies were performed as described below.

Figure 4A:
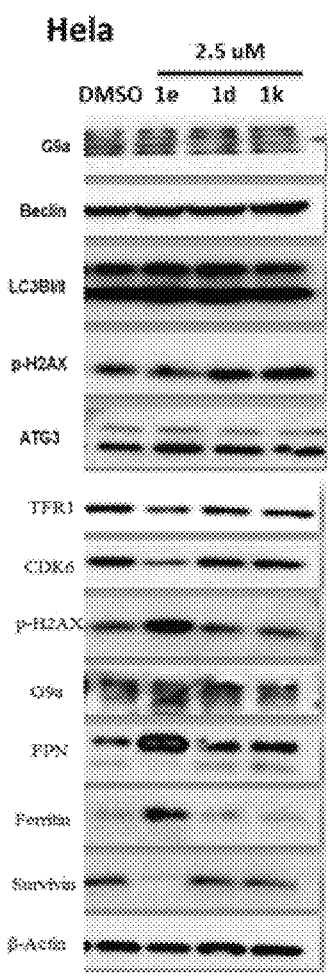
FIG. 4A. depicts an image of the Western blot analysis: The expression profile of autophagy- and iron metabolism-related proteins in the treated and control cells of Hela in accordance with an embodiment of the present invention.
Figure 4B:
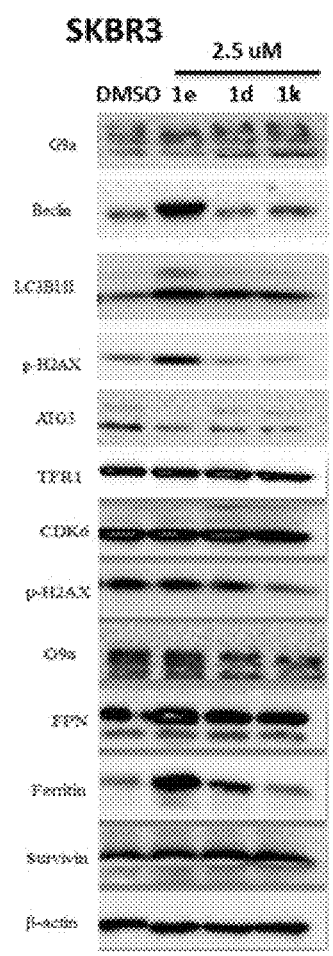
FIG. 4B. depicts an image of the Western blot analysis: The expression profile of autophagy- and iron metabolism-related proteins in treated and control cells of SKBR3 in accordance with an embodiment of the present invention.

Western blot analysis: Western blot analysis was performed to evaluate the expression profile of autophagy- and iron metabolism-related proteins in treated and control cells of Hela and SKBR3 cells. As a result, it was found that compounds 1d, 1e and 1k upregulate the expression and metabolism of the autophagy marker LC3B1/II in Hela cells (as shown in FIG. 4A). Furthermore, compounds 1d and 1k induce the expression of the DNA damage marker pH2AX in Hela cells (as shown in FIG. 4A). Moreover, compound 1e inhibits the expressions of many genes in Hela cells which include the cell cycle marker CDK6, the cell survival marker, the cellular iron exporter protein Ferroportin (FPN) and the cellular iron storing protein Ferritin heavy chain (FTH1). Additionally, compound 1e induced the expression of BECLIN-1 (inducer of ferroptosis), LC3B1/II (a marker of autophagy), pH2AX (a marker of DNA damage) and Ferritin (FTH1) (cellular iron storing protein) in SKBR3 cells (as shown in FIG. 4B).

Figure 5A:
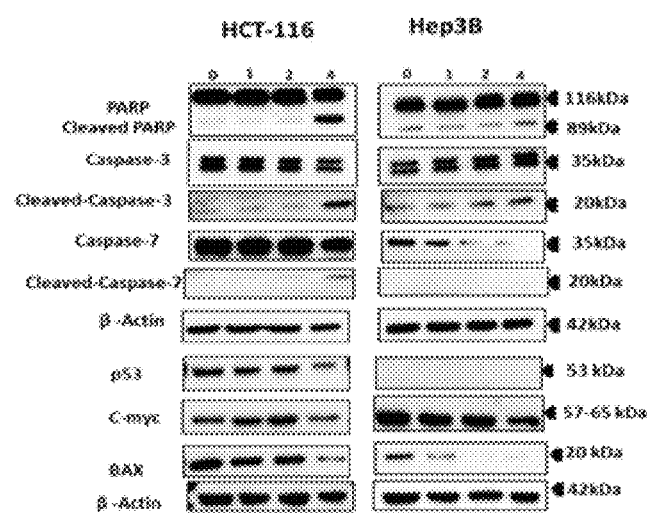
FIG. 5A. depicts an image of the Immunoblots of the indicated proteins in HCT-116 and Hep3B treated cells with 1, 2, 4 µM of 1f in accordance with an embodiment of the present invention.
Figure 5B:
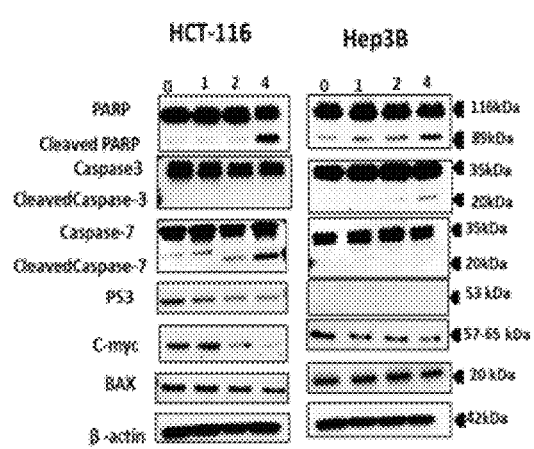
FIG. 5B. depicts an image of the Immunoblots of the indicated proteins in HCT-116 and Hep3B treated cells with 1, 2, 4 µM of 1h.

Induction of Apoptosis: To explore the mechanism by which the compounds are inducing cancer death, the best hits on HCT-116 and Hep3B cell lines were selected for further study, which are compounds 1f (as shown in FIG. 5A), and 1h (as shown in FIG. 5B). Their effect on different apoptotic biomarkers as well on tumor suppressor genes and oncogenes was investigated using Western blot analysis. After treating the cells with concentrations of the compounds below and above their IC$_{50}$'s, it was noted that the compounds are showing evidence of apoptosis, which is marked by the cleavage of the executioner caspases, caspase7, and caspase-3. The cleavage of caspases was so clear at 4 μM concentration. In addition, both compounds showed PARP cleavage in both cell lines, which provided further evidence of apoptosis as a mechanism of cell death. Interestingly, the induction of apoptosis was independent of p53 activation since the levels of p53 proteins were decreased at higher concentrations of the test compounds in HCT-116 cells. The independence on p53 to induce apoptosis was confirmed in Hep3B cells, which originally lacks p53 expression and showed a similar profile of cell death on treatment by both compounds. The treated cells exhibited decreased levels of BAX, which was parallel to the decreased levels of p53. Since BAX expression is directly regulated by p53, these results confirmed the decrease in p53. Furthermore, the test compounds showed their ability to downregulate the oncogene, c-Myc in a dose-dependent manner which supports their promise as anticancer agents.

Example 4: Activity Against MDR Gram-Positive Bacteria: Methicillin-Resistant *Staphylococcus Aureus* (MRSA) and Vancomycin Intermediate-Resistant *Staphylococcus aureus* (VISA)

Based on the results shown in Table 4, 12 representative compounds were tested on a panel of 6 MRSA strains. One of these strains was intermediately resistant to vancomycin (MIC: 8 μg/mL) while the rest of the strains were susceptible to this antibiotic (MIC: 1 μg/mL).

TABLE 4

MIC values (μg/mL) for the selected compounds tested on Gram-positive bacteria, including 3 clinical isolates of methicillin-resistant *Staphylococcus aureus* (MRSA) and 3 reference MRSA strains (ATCC33591, ATCC33592 and ATCC700699). The last strain is intermediately resistant to vancomycin (VISA).

| Compound | MIC (μg/mL) | | | | | |
|---|---|---|---|---|---|---|
| | MRSA-1 (clinical isolate) | MRSA-2 (clinical isolate) | MRSA-3 (clinical isolate) | MRSA-ATCC33591 | MRSA-ATCC33592 | MRSA-ATCC700699 (VISA) |
| 1c | 3.125 | 3.125 | 3.125 | 6.25 | 6.25 | 6.25 |
| 1d | 3.125 | 3.125 | 3.125 | 3.125 | 3.125 | 3.125 |
| 1e | 1.56 | 1.56 | 1.56 | 3.125 | 3.125 | 3.125 |
| 1f | 6.25 | 6.25 | 6.25 | 6.25 | 6.25 | 6.25 |
| 1g | 1.56 | 1.56 | 1.56 | 1.56 | 1.56 | 1.56 |
| 1h | 1.56 | 1.56 | 1.56 | 1.56 | 1.56 | 1.56 |
| 1i | 1.56 | 3.125 | 3.125 | 3.125 | 3.125 | 1.56 |
| 1j | 1.56 | 3.125 | 3.125 | 3.125 | 3.125 | 3.125 |
| 1k | 1.56 | 1.56 | 1.56 | 3.125 | 3.125 | 3.125 |
| 1l | 1.56 | 3.125 | 3.125 | 3.125 | 3.125 | 3.125 |
| 1m | 3.125 | 3.125 | 3.125 | 6.25 | 6.25 | 6.25 |
| 1n | 3.125 | 3.125 | 3.125 | 6.25 | 6.25 | 6.25 |
| Vancomycin | 1 | 1 | 1 | 1 | 1 | 8 * |
| Gentamicin | 50 | 0.625 | 0.625 | 2.5 | >500 | 500 |
| Amikacin | 16 | 8 | 2 | 50 | 50 | 100 |
| Ciprofloxacin | 32 | 16 | 2 | 0.3 | 0.3 | 16 |

As shown in Table 2, the compounds were active against all the 6 MRSA strains (MIC: 1.56-6.25 μg/mL). All the compounds were active against VISA strain intermediately resistant to vancomycin (ATCC 700699) with MIC range between 1.56 to 6.25 μg/mL, which is less than the MIC of vancomycin (8 μg/mL), the drug of choice for treating infections caused by MRSA. Compounds 1g and 1h showed the most potent activity with MIC of 1.56 μg/mL against all the tested strains. These compounds (1g and 1h) exhibited MIC of 1.56 μg/mL which is similar to the MIC value of vancomycin (1 μg/mL) in strains MRSA-1, MRSA-2, MRSA-3, ATCC 33591 and ATCC 33592. The MIC of the same compounds (1.56 μg/mL) was ~5 times less than the MIC of vancomycin (8 μg/mL) on VISA strain intermediately resistant to vancomycin (ATCC 700699). The strains tested exhibited variable resistance profiles to other antibiotics, including aminoglycosides (MIC: 0.625-≥500 μg/mL for gentamicin and 2-100 μg/mL for amikacin) and fluoroquinolones (MIC: 0.3-32 μg/mL for ciprofloxacin). From the MICs, we noticed that some of the tested strains were highly resistant to these antibiotics. Nevertheless, our compounds are effective with significant low MICs (Table 2, strain ATCC 700699).

Example 5: Activity Against MDR Gram-Negative Bacteria (MDR *Escherichia coli* and *Acinetobacter baumannii*)

The compounds of this invention tested for potential antibacterial activities against Gram-negative bacteria from 2 species, including *Escherichia coli* and *Acinetobacter baumannii*.

As shown in Table 5, selected compounds were tested for activity against five Gram-negative bacteria, three of them were multidrug-resistant (MDR) including, New Delhi metallo-beta-lactamase (NDM-1) positive, carbapenem-resistant *E. coli* (ATCC BAA2469), extended-spectrum beta-lactamase (ESBL) producing, colistin-resistant *E. coli* (CDC-AR-0346) and carbapenem-resistant *Acinetobacter baumannii* (ATCC BAA1605), in addition to two non-MDR bacteria from the same species namely *E. coli* (ATCC 25922) *Acinetobacter baumannii* (ATCC 19606).

TABLE 5

MIC values (μg/mL) for the selected compounds tested on 5 Gram-negative bacteria from 2 species (*Escherichia coli* and *Acinetobacter baumannii*).

| Compound | MIC (μg/mL) | | | | |
|---|---|---|---|---|---|
| | E. coli ATCC25922 * | E. coli ATCC BAA2469 (NDM-1 carbapenem-resistant) | E. coli CDC-AR-0346 (ESBL #, colistin resistant) | Acinetobacter baumannii ATCC 19606 * | Acinetobacter baumannii ATCC BAA1605 (carbapenem-resistant) |
| 1e | 6.25 | 12.5 | 12.5 | 6.25 | 12.5 |
| 1f | 12.5 | 25 | 25 | 12.5 | 25 |
| 1g | 6.25 | 6.25 | 12.5 | 6.25 | 6.25 |
| 1h | 12.5 | 12.5 | 12.5 | 6.25 | 25 |
| 1i | 12.5 | 12.5 | 25 | 6.25 | 12.5 |
| 1k | 6.25 | 25 | 50 | 6.25 | 50 |
| Meropenem | <0.02 | 25 | <0.2 | 0.6 | 12.5 |
| Colistin | 0.2 | 1.25 | 6.25 | 1.25 | 1.25 |
| Gentamicin | 0.625 | >1000 | >1000 | 10 | 125 |
| Amikacin | 2.5 | >1000 | >1000 | 10 | 1.25 |

TABLE 5-continued

MIC values (μg/mL) for the selected compounds tested on 5 Gram-negative
bacteria from 2 species (Escherichia coli and Acinetobacter baumannii).

| | MIC (μg/mL) | | | | |
|---|---|---|---|---|---|
| Compound | E. coli ATCC25922 * | E. coli ATCC BAA2469 (NDM-1 carbapenem-resistant) | E. coli CDC-AR-0346 (ESBL #, colistin resistant) | Acinetobacter baumannii ATCC 19606 * | Acinetobacter baumannii ATCC BAA1605 (carbapenem-resistant) |
| Ciprofloxacin | <0.02 | 100 | 16 | 0.625 | 50 |
| Cefotaxime | 0.03 | 250 | >1000 | 20 | 1000 |
| Ceftriaxone | 0.03 | 500 | >1000 | 20 | >1000 |

* not MDR;
resistant to first, second, third and fourth generation cephalosporines As shown in Table 3, the compounds were active against all the three *Escherichia coli* strains (MIC: 6.25-50 μg/mL). Most of the compounds were more active on the non-MDR strain (ATCC25922) with MICs range between 6.25 to 12.5 μg/mL. The MIC values on the MDR strains range between 6.25-25 μg/mL for *E. coli* (ATCC BAA2469) and 12.5-50 μg/mL for *E. coli* (CDC-AR-0346). Strain *E. coli* (ATCC BAA2469) is resistant to carbapenems including meropenem (MIC: 25 μg/mL); however, some of the tested compounds (1e, 1g, 1h, and 1i) had MIC values 2 to 4-fold below this value (6.25-12.5 μg/mL). The compounds were also active on *E. coli* (CDC-AR-0346) which is an extended-spectrum beta-lactamase (ESBL) producing bacteria (resistant to first, second, third and fourth generation cephalosporines) and also resistant to colistin. MICs (12.5 μg/mL) of some compounds (1e, 1g and 1h) were 2-fold higher than that of colistin (6.25 μg/mL).

Both MDR *E. coli* strains were highly resistant to cephalosporines (MIC: 250-≥1000 μg/mL for cefotaxime and ceftriaxone), aminoglycosides (MIC: >1000 μg/mL for gentamicin and amikacin) and fluoroquinolones (MIC: 16-100 μg/mL for ciprofloxacin). Despite the high resistance of these strains, MICs of our compounds are significantly lower than the MICs of these antibiotics.

The compounds were also active on both non-MDR *Acinetobacter baumannii* (ATCC 19606; MIC of 6.25-12.5 μg/mL) and on the MDR *Acinetobacter baumannii* (ATCC BAA1605; MIC of 6.25-50 μg/mL). The latter strain is resistant to carbapenems including meropenem (MIC: 12.5 μg/mL). One of the compounds tested (1g) had MIC, which is 2-fold below that of meropenem (MIC: 6.25 μg/mL). On the other hand, this strain was also highly resistant to other antibiotics including cephalosporins (MIC: ≥1000 μg/mL for cefotaxime and ceftriaxone), aminoglycosides (MIC: 125 μg/mL for gentamicin) and fluoroquinolones (MIC: 50 μg/mL for ciprofloxacin). MICs of our compounds are significantly lower than the MICs for these antibiotics.

Based on the results above, the compounds are expected to be useful as antibiotics for both Gram-positive and Gram-negative bacteria. The data suggest that, in general, Gram-positive bacteria (MIC: 1.56-6.25 μg/mL) are more sensitive to our compounds than Gram-negative bacteria (MIC: 6.25-50 μg/mL).

General Materials and Methods of the Present Disclosure

In the present invention unless otherwise stated, the following materials, techniques, and methods were used in the experiments described herein.

Chemistry

Purchased chemical reagents and anhydrous solvents were used without further purification. Solvents for extraction and column chromatography were distilled prior to use. TLC analysis was performed with silica gel plates (0.25 mm, 60 F254) using iodine and a UV lamp for visualization. $^1$H and $^{13}$C NMR experiments were performed on a 500 MHz instrument. Chemical shifts are reported in parts per million (ppm) downstream from the internal tetramethylsilane standard. Spin multiplicities are described as s (singlet), bs (broad singlet), d (doublet), dd (double doublet), t (triplet), q (quartet), or m (multiplet). Coupling constants are reported in Hertz (Hz). ESI mass spectrometry was performed on a Q-TOF high-resolution mass spectrometer or Q-TOF Ultim LC-MS.

Biology

Cell culture: In this study five different cancer cell lines were used, human lung carcinoma (A549), human breast adenoma (MCF-7), Cervical carcinoma (Hela), hepatocellular carcinoma (Hep3B), and colorectal adenocarcinoma (HCT-116). These cells were obtained from the European Collection of Cell Cultures (ECACC, UK). Hep3B cells were maintained in Dulbecco's Modified Eagle Medium (DMEM: Sigma-Aldrich), and the four other cell lines were maintained in Roswell Park Memorial Institute medium (RPMI, Sigma-Aldrich, St. Louis, Mo., USA), which was supplemented with 10% fetal bovine serum (FBS, Sigma-Aldrich) and 1% penicillin/streptomycin (Sigma-Aldrich). Cells were incubated all the time at 37° C. in a humidified atmosphere of 5% $CO_2$.

Cell viability studies: Cell viability was assessed using the MTT assay as described before. In brief, all cancer cell lines were seeded at a density of $4 \times 10^4$/well in 96 well flat-bottom plates. After 24 h from seeding, cells were treated with the synthesized compounds and left for an incubation period of 48 h. Upon reaching the indicated time point, the media was removed and replaced with 200 μL fresh media containing 0.5 mg/mL of MTT tetrazolium dye (Sigma-Aldrich). Cells were then incubated with MTT solution for 2 h at 37° C. The resultant formazan crystals were dissolved in 200 μl/well of DMSO and absorbance was measured at 570 nm using a microplate reader (Thermo Scientific).

Colony formation assay: Human Normal epithelial cells, SKBR3, and SKOV3 cells were treated with 1d, 1e and 1k compounds with indicated concentrations for 48 h. Then cells were fixed with colony fixation solution (Acetic acid/Methanol (1:7) vol/vol) at room temperature. 15 minutes later fixation solution was removed and cells were washed again carefully with 1×PBS. Cells were stained with 0.5% crystal violet at room temperature for 20 minutes. Crystal violet was removed and cells were washed carefully 3 times with distilled water to remove excess dye. Colony growth was visualized by crystal violet staining.

DAPI staining: SKBR3 and SKOV3 cells were treated with indicated compounds. After 48 h of treatment, the media were removed from cell lines and cells were washed with 1× cold PBS. Cells were fixed with (Acetic acid/Methanol (1:7) vol/vol)) solution for 15 minutes at RT and then washed with 1× cold PBS. Permeabilization was performed with 0.1% Triton X-100 for 5 minutes and then cells were washed with 1× cold PBS. Cells were stain with DAPI solution for 15 minutes at RT and then cells were washed 3 times with 1× cold PBS. Images were taken using a fluorescence microscope.

Western blotting (apoptotic biomarkers, tumor suppressor genes and oncogenes): Hep3B and HCT-116 cells were treated with 1f and 1h compounds with increasing concentrations from 1 to 4 µM for 48 h. After reaching the time point, proteins were extracted from the collected cells after their lyses, and protein quantification was performed using a Detergent compatible (DC) protein assay kit (Bio-Rad) following the manufacturer's instructions. 12% SDS-polyacrylamide gels were used to separate the proteins, following the proteins were transferred onto nitrocellulose membrane using a semi-dry transfer cell. After transfer, membranes were incubated with primary antibodies and the incubation was left overnight at 4° c. The following antibodies were implicated: anti-β actin (Cell Signalling #4970), anti-caspase3 (Cell Signalling #14220), anti-caspase-7 (Cell Signalling33 #9532), anti-PARP (Cell Signalling #9532), anti-P53 (Cell Signalling #2527), anti-C-myc (Cell Signalling #18583), and anti-BAX (#5023). Finally, membranes were incubated with secondary conjugated with horseradish peroxidase. The indicated proteins were detected by chemiluminescence.

Western Blotting (autophagy- and iron metabolism-related proteins): Cells were grown in DMEM supplemented with 10% FBS and 1×PEST (Penicillin and streptomycin antibiotics) at 37° C. in incubator having humidified atmosphere with 5% $CO_2$. The media were removed and cells were washed twice with 1× cold PBS. Cells lysis was performed with RIPA lysis buffer containing (150 mM sodium chloride, 1.0% NP-40, 0.1% SDS, 50 mM Tris pH 8.0, 0.5% sodium deoxycholate supplemented with protease inhibitors cocktail). Cells were kept on icebox during the lysis process. Cold lysis buffer was added to each well directly and then cells were scraped and collected in 1.5 ml Eppendorf tube. Cell lysis was kept on icebox for 20 minutes and then centrifuged at 4° C. for 10 minutes. The supernatant was collected and the pellet was discarded. After, protein quantification, samples were boiled in 5× loading buffer at 95° C. for 5 minutes. After completion of the gel running and transfer process, the membrane was stained with ponceau solution. After that, the membrane was washed with 1×TBST and then blocked in 5% non-fat dry milk for 1 hr at room temperature. The membrane was washed 3 times with 1×TBST and then incubated with indicated primary antibodies at 4° C. overnight. Primary antibodies were removed; the membrane was washed 3 times with 1×TBST and then incubated with secondary antibodies for 2 h at room temperature. Secondary antibodies were diluted in 5% non-fat dry milk in 1× TB ST. After removal of the secondary antibody, the membrane was washed 3 times with 1×TBST. The membrane was incubated in ECL solution and the signal was developed using Gel Doc system from Biorad.

Antibacterial activity: The compounds were tested for the minimum inhibitory concentrations (MIC), which is the lowest concentration of a chemical required to inhibit visible microbial growth following overnight incubation. MIC values were determined using broth microdilution method according to the Clinical and Laboratory Standards Institute guidelines (CLSI, 2015, M07-A10). Mueller-Hinton broth was used as a culture medium in all the experiments. Exponentially growing bacterial cells were prepared in Mueller-Hinton broth at a concentration of approximately $5×10^5$ CFU/mL. Two-fold serial dilutions of the test compound (8 concentrations ranged between 100-0.78 µg/mL) were tested. Vancomycin, gentamicin, amikacin and ciprofloxacin were used as quality control for Gram-positive bacteria, while colistin, meropenem, gentamicin, amikacin, ciprofloxacin, cefotaxime and ceftriaxone were used as quality controls for Gram-negative bacteria. In each experiment, solvent (DMSO) was used as a negative control, un-treated control (composing of bacteria in Mueller-Hinton broth) was used as a growth control, blank (culture media alone) was used as sterility control. The 96-well microplate with the test compounds was incubated overnight at 37° C. Turbidity in wells indicated bacterial growth. The MIC was recorded as the lowest concentration of a compound that completely inhibited any visible bacterial growth after overnight incubation.

The compounds were tested on six MDR Gram-positive bacteria including three clinical isolates of methicillin-resistant *Staphylococcus aureus* (MRSA-1, MRSA-2 and MRSA-3) and three reference MRSA strains (ATCC33591, ATCC33592 and ATCC700699). They were also tested on three MDR Gram-negative bacteria including New Delhi metallo-beta-lactamase (NDM-1) positive, carbapenem-resistant *E. coli* (ATCC BAA2469), extended-spectrum beta-lactamase (ESBL) producing, colistin-resistant *E. coli* (CDC-AR-0346) and carbapenem-resistant *Acinetobacter baumannii* (ATCC BAA1605), in addition to two non-MDR bacteria from the same species, namely *E. coli* (ATCC 25922) *Acinetobacter baumannii* (ATCC 19606).

While the invention has been illustrated and described in detail in the drawings and foregoing description, the same is to be considered as illustrative and not restrictive in character, it being understood that only some embodiments have been shown and described and that all changes and modifications that come within the spirit of the inventions are desired to be protected. It should be understood that while the use of words such as preferable, preferably, preferred, more preferred or exemplary utilized in the description above indicate that the feature so described may be more desirable or characteristic, nonetheless may not be necessary and embodiments lacking the same may be contemplated as within the scope of the invention, the scope being defined by the claims that follow. In reading the claims, it is intended that when words such as "a," "an," "at least one," or "at least one portion" are used there is no intention to limit the claim to only one item unless specifically stated to the contrary in the claim.

Although only a few example embodiments have been described in detail above, many changes, modifications, variations and other uses and applications of the subject invention will become apparent to those skilled in the art after considering this specification and the accompanying drawings, which disclose the preferred embodiments thereof. All such changes, modifications, variations and other uses and applications, which do not depart from the spirit and scope of the invention, are deemed to be covered by the invention, which is to be limited only by the claims which follow.

The invention claimed is:

1. A compound having the following general formula (A), (A'), or (A"):

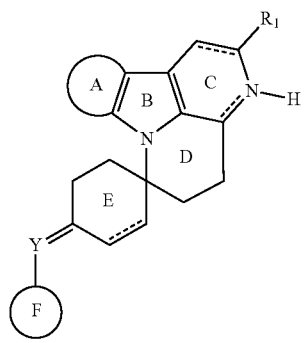
(A)

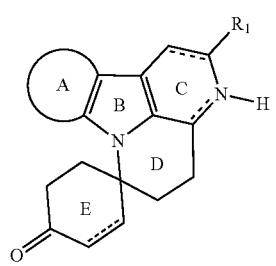
(A')

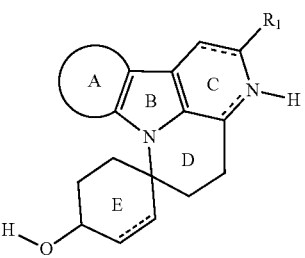
(A")

wherein:

is a phenyl ring which may be unsubstituted or substituted with 1, 2, 3 or 4 substituents independently selected from the group consisting of: a halogen atom, CN, $R^2$, $OR^2$, $SR^2$, $N(R^2)_2$, $C(O)R^2$, $C(O)OR^2$, $NR^2C(O)R^2$, $C(O)N(R^2)_2$, $SO_2R^2$, $NR^2SO_2R^2$, and $SO^2N(R^2)_2$;

is a phenyl ring which may be unsubstituted or substituted with 1, 2, 3, 4 or 5 substituents independently selected from the group consisting of: a halogen atom, CN, $NO_2$, $OCX_3$, $C(O)R^2$, $C(O)OR^2$, $NR^2C(O)R^2$, $C(O)N(R^2)_2$, $SO_2R^2$, $NR^2SO_2R^2$, and $SO_2N(R^2)_2$;

$R^1$ is hydrogen or an unsubstituted or substituted alkyl, aryl, or heteroaryl group or $R^1$ is selected from the group consisting of: $C(O)OR^2$, CN, $N(R^2)_2$, $C(O)R^2$, $C(O)N(R^2)_2$, $SO_2R^2$, $SO_2N(R^2)_2$, and $PO_2R^2$;

X is selected from the group consisting of chlorine, fluorine, bromine, and iodine;

Y is —N—$NR_2$; and $R^2$ is hydrogen or an optionally substituted group selected from the group consisting of a C1-6 aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur; or a pharmaceutically acceptable salt, thereof.

2. The compound as claimed in 1, wherein $R^2$ is selected from the group consisting of —$CX_3$, —$CHX_2$, and $CH_2X$, wherein X is chlorine, fluorine, bromine, or iodine.

3. A process for preparing the compound of general formula (A), (A'), or (A") of claim 1, the process comprising the following steps:

reacting a compound of general formula

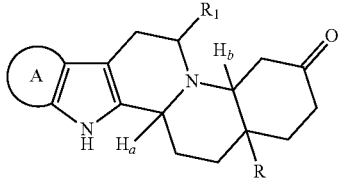
(I)

with a compound of general formula

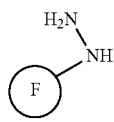
(II)

in an acetic acid solvent to form a mixture;
heating the mixture between 40° C. to 150° C. to obtain a crude material; and
removing the solvent to yield the compound of general formula (A), (A'), or (A"),
wherein in formula (I) and formula (II):

is a phenyl ring which may be unsubstituted or substituted with 1, 2, 3 or 4 substituents independently selected from the group consisting of: a halogen atom, CN, $R^2$, $OR^2$, $SR^2$, $N(R^2)_2$, $C(O)R^2$, $C(O)OR^2$, $NR^2C(O)R^2$, $C(O)N(R^2)_2$, $SO_2R^2$, $NR^2SO_2R^2$, and $SO^2N(R^2)_2$;

is a phenyl ring which may be unsubstituted or substituted with 1, 2, 3, 4 or 5 substituents independently selected from the group consisting of: a halogen atom, CN, $NO_2$, $OCX_3$, $C(O)R^2$, $C(O)OR^2$, $NR^2C(O)R^2$, $C(O)N(R^2)_2$, $SO_2R^2$, $NR^2SO_2R^2$, and $SO_2N(R^2)_2$;

R denotes halogen atom, $R^2$, $OR^2$, $SR^2$, $N(R^2)_2$, $NR^2C(O)R^2$, $C(O)N(R^2)_2$, $SO_2R^2$, $NR^2SO_2R^2$, $SO_2N(R^2)_2$;

$R^1$ is hydrogen or an unsubstituted or substituted alkyl, aryl, or heteroaryl group or $R^1$ is selected from the group consisting of: $C(O)OR^2$, CN, $N(R^2)_2$, $C(O)R^2$, $C(O)N(R^2)_2$, $SO_2R^2$, $SO_2N(R^2)_2$, and $PO_2R^2$;

$R^2$ is hydrogen or an optionally substituted group selected from the group consisting of: a C1-6 aliphatic group; a monocyclic 3-8 membered saturated, partially unsaturated, or aryl ring having 0-4 heteroatoms independently selected from nitrogen, oxygen, or sulfur; a bicyclic 8-10 membered saturated, partially unsaturated, or aryl ring having 0-5 heteroatoms independently selected from nitrogen, oxygen, or sulfur; and the stereochemical relation between Ha, Hb, R and R1 is either in the form of pure enantiomers, diastereoisomers or racemic mixtures; and X is selected from the group consisting of chlorine, fluorine, bromine, and iodine.

4. The process of claim 3, wherein the mole ratio of compound of formula (I) to compound of formula (II) is about 1:1 to about 1:2.

5. The process of claim 3, further comprising using column chromatography with a mobile phase selected from MeOH/DCM or EtOAc/hexane to purify the compound of general formula (A), (A'), or (A").

6. The process of claim 3, further comprising recrystallizing the compound of general formula (A), (A'), or (A") using EtOAc or MeOH.

7. The process of claim 3, further comprising precipitating the compound of general formula (A), (A'), or (A") using a combination of solvents selected from EtOAc/diethylether or EtOAc/hexane.

8. The compound of general formula (A), (A'), or (A") as claimed in claim 1, selected from one of the following chemical structures, including enantiomers and, diastereoisomers thereof:

1a

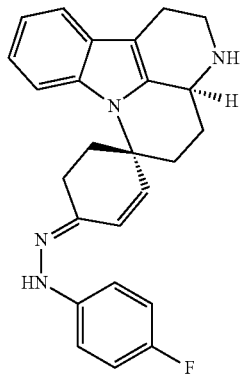

1b

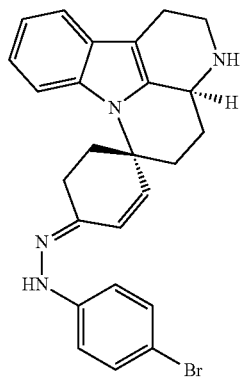

1c

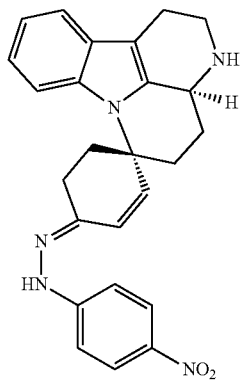

1d

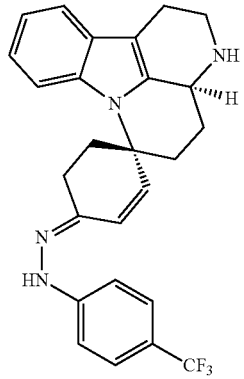

1e

-continued
1f
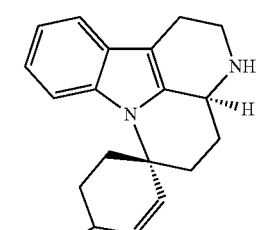
1g
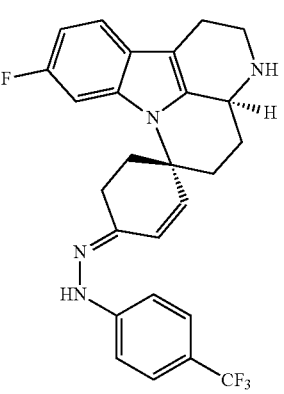
1h
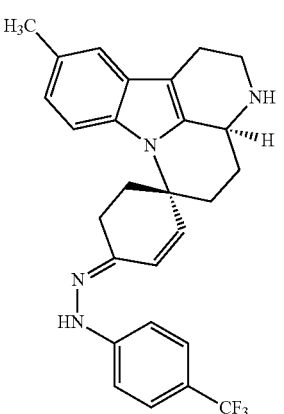
1i
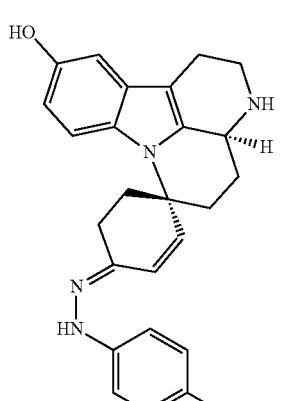
-continued
1j
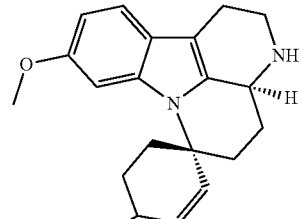
1k
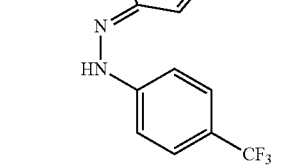
1l
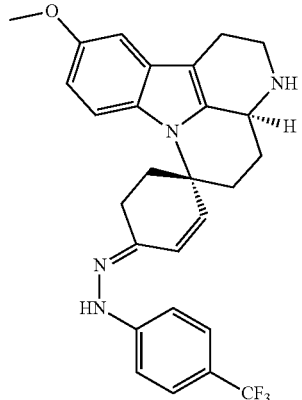
1m
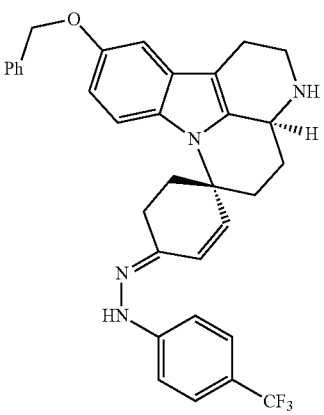

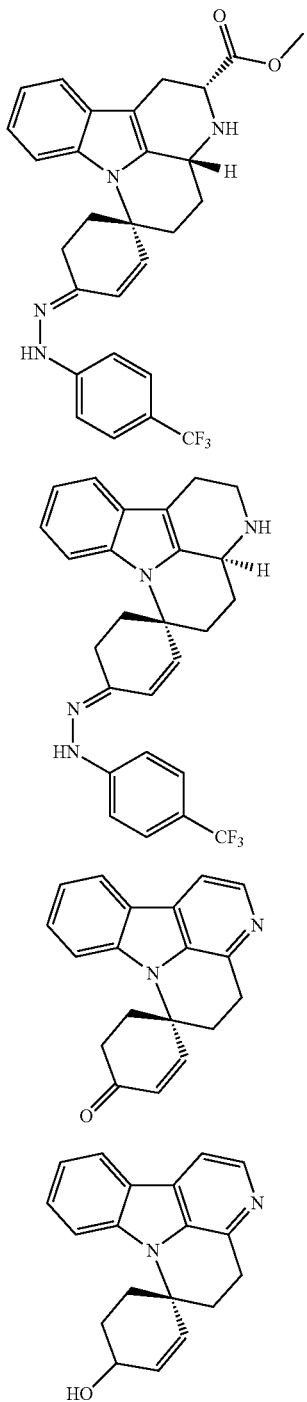

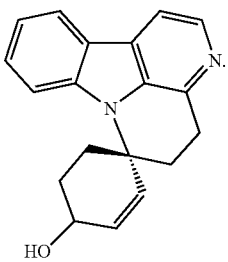

9. A method of treating a subject suffering from cancer, the method comprising administering a pharmaceutical composition comprising one or more compounds as claimed in claim 8 as an active ingredient, or a pharmaceutically acceptable salt thereof and pharmaceutically acceptable carrier to the subject.

10. A method of treating a subject suffering from cancer comprising administering to the subject one or more compounds of claim 8.

11. The compound of general formula (A), (A'), or (A") as claimed in claim 1 for use in preparation of a medicament having anticancer activity, wherein the cancer cell lines are selected from the group consisting of colorectal, liver, lung, breast, stomach and cervical.

12. The method as claimed in claim 10, wherein the cancer cell lines are HCT-116, Hep3b, A549, MCF-7, SKOV3, SKBR3, MDA-MB-231, MDA-MB-468, JIMT1, AGS and Hela.

13. The compound of general formula (A), (A'), or (A") as claimed in claim 1 for use in preparation of a medicament having antibacterial activity.

14. The compound of claim 13, wherein the medicament has antibacterial activity against a bacterial species selected from the group consisting of Gram-positive multidrug resistant bacteria, Gram-negative multidrug resistant bacteria and Gram-negative non-multidrug resistant bacteria.

15. The compound of claim 14, wherein the Gram-positive multidrug resistant bacteria are methicillin resistant *Staphylococcus aureus* ATCC33591, ATCC33592 and ATCC700699.

16. The compound of claim 14, wherein the Gram-negative multidrug resistant bacteria are carbapenem-resistant *E. coli*, colistin resistant *E. coli* and carbapenem-resistant *Acinetobacter baumannii*.

17. The compound of claim 14, wherein the Gram-negative non-multidrug resistant bacteria are *E. coli* and *Acinetobacter baumannii*.

* * * * *